United States Patent [19]
Goodman et al.

[11] Patent Number: 6,046,015
[45] Date of Patent: Apr. 4, 2000

[54] MODULATING ROBO: LIGAND INTERACTIONS

[75] Inventors: Corey S. Goodman; Thomas Kidd, both of Berkeley; Katja Brose; Marc Tessier-Lavigne, both of San Francisco, all of Calif.

[73] Assignee: The Regents of the University of California, Oakland, Calif.

[21] Appl. No.: 09/191,647

[22] Filed: Nov. 13, 1998

Related U.S. Application Data

[60] Provisional application No. 60/081,057, Apr. 7, 1998, and provisional application No. 60/065,544, Nov. 14, 1997.

[51] Int. Cl.[7] .............................. G01N 33/53; C07K 7/08; C07K 14/47; C12N 5/02
[52] U.S. Cl. .......................... 435/7.8; 435/375; 530/324; 530/325; 530/326; 530/350
[58] Field of Search .................................... 530/300, 324, 530/325, 326, 350; 435/375, 7.8

[56] References Cited

PUBLICATIONS

Wilson et al, Nature, vol. 368: pp. 32–38, Mar. 1994.

*Primary Examiner*—Terry McKelvey
*Attorney, Agent, or Firm*—Richard Aron Osman

[57] ABSTRACT

Disclosed are methods and compositions for identifing agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the agent modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

21 Claims, No Drawings

MODULATING ROBO: LIGAND INTERACTIONS

CROSS-REFERENCE TO RELATED APPLICATIONS

This application claims the benefit of U.S. Provisional Application No. 60/081,057, filed Apr. 7, 1998 and U.S. Provisional Application No. 60/065,544, filed Nov. 14, 1997.

The research carried out in the subject application was supported in part by NIH grant NS18366. The government may have rights in any patent issuing on this application.

INTRODUCTION

1. Field of the Invention

The field of this invention is methods for modulating nerve cell function.

2. Background

In the developing CNS, most growth cones confront the midline at one or multiple times during their journey and make the decision of whether to cross or not to cross. This decision is not a static one but rather changes according to the growth cone's history. For example, in the Drosophila ventral nerve cord, about 10% of the intemeurons project their axons only on their own side, in some cases extending near the midline without crossing it The other 90% of the interneurons first project their axons across the midline and then turn to project longitudinally on the other side, often extending near the midline. These growth cones, having crossed the midline once, never cross it again, in spite of their close proximity to the midline and the many commissural axons crossing it. This decision to cross or not to cross is not unique to Drosophila but is common to a variety of midline structures in all bilaterally symmetric nervous systems.

What midline signals and growth cone receptors control whether growth cones do or do not cross the midline? After crossing once, what mechanism prevents these growth cones from crossing again? A related issue concerns the nature of the midline as an intermediate target. If so many growth cones find the midline such an attractive structure, why do they cross over it rather than linger? Why do they leave the midline?

One approach to find the genes encoding the components of such a system is to screen for mutations in which either too many or too few axons cross the midline. Such a large-scale mutant screen was previously conducted in Drosophila, and led to the identification of two key genes: commissureless (comm) and roundabout (robo) (Seeger et al., 1993; reviewed by Tear et al., 1993). In comm mutant embryos, commissural growth cones initially orient toward the midline but then fail to cross it and instead recoil and extend on their own side. robo mutant embryos, on the other hand, display the opposite phenotype in that too many axons cross the midline; many growth cones that normally extend only on their own side instead now project across the midline and axons that normally cross the midline only once instead appear to cross and recross multiple times (Seeger et al, 1993; present disclosure). Double mutants of comm and robo display a robo-like phenotype.

How do comm and robo function to control midline crossing? Neither the initial paper on these genes (Seeger et al., 1993) nor the cloning of comm (Tear et al., 1996) resolved this question. comm encodes a novel surface protein expressed on midline cells. In fact, the comm paper (Tear et al., 1996) ended with the hope that future work would ". . . help shed some light on the enigmatic function of Comm."

U.S. Ser. No. 08/971,172 (Robo, A Novel Family of Polypeptides and Nucleic Acids, by inventors: Corey S. Goodman, Thomas Kidd, Kevin J. Mitchell and Guy Tear) discloses the cloning and characterization of robo in various species including Drosophila; Robo polypeptides and polypeptide-encoding nucleic acids are also disclosed and their genbank accession numbers referenced in Kidd et al. (1998) Cell 92, 205–215. robo encodes a new class of guidance receptor with 5 immunoglobulin (Ig) domains, 3 fibronectin type III domains, a transmembrane domain, and a long cytoplasmic domain. Robo defines a new subfamily of Ig superfamily proteins that is highly conserved from fruit flies to mammals. The Robo ectodomains, and in particular the first two Ig domains, are highly conserved from fruit fly to human, while the cytoplasmic domains are more divergent. Nevertheless, the cytoplasmic domains contain three highly conserved short proline-rich motifs which may represent binding sites for SH3 or other binding domains in linker or signaling molecules.

For those axons that never cross the midline, Robo is expressed on their growth cones from the outset; for the majority of axons that do cross the midline, Robo is expressed at high levels on their growth cones only after they cross the midline. Transgenic rescue experiments in Drosophila reveal that Robo can function in a cell autonomous fashion, consistent with it functioning as a receptor. Thus, in Drosophila, Robo appears to function as the gatekeeper controlling midline crossing; growth cones expressing high levels of Robo are prevented from crossing the midline. Robo proteins in mammals function in a similar manner in controlling axon guidance.

U.S. Ser. No. 60/065,54 (Methods for Modulating Nerve Cell Function, by inventors: Corey S. Goodman, Thomas Kidd, Guy Tear, Claire Russell and Kevin Mitchell) discloses ectopic and overexpression studies revealing that Comm down-regulates Robo expression, demonstrating that Comm functions to suppress the Robo-mediated midline repulsion. These results show that the levels of Comm at the midline and Robo on growth cones are tightly intertwined and dynamically regulated to assure that only certain growth cones cross the midline, that those growth cones that cross do not linger at the midline, and that once they cross they never do so again.

Relevant Literature

Seeger, M., Tear, G., Ferres-Marco, D. and Goodmnan C. S. (1993) Neuron 10, 409–426; Tear G., et al. (1996) Neuron 16, 501–514; Rothberg et al. (1990) Genes Dev 4, 2169–2187; Kidd et al. (1998) Cell 92, 205–215.

SUMMARY OF THE INVENTION

The invention provides methods and compositions relating to vertebrate Slit1 and Slit2, collectively vertebrate Slit) polypeptides, related nucleic acids, polypeptide domains thereof having vertebrate Slit-specific structure and activity, and modulators of vertebrate Slit function. Vertebrate Slit polypeptides can regulate cell, especially nerve cell, function and morphology. The polypeptides may be produced recombinantly from transformed host cells from the subject vertebrate Slit polypeptide encoding nucleic acids or purified from mammalian cells. The invention provides isolated vertebrate Slit hybridization probes and primers capable of specifically hybridizing with natural vertebrate Slit genes, vertebrate Slit-specific binding agents such as specific antibodies, and methods of making and using the subject compositions in diagnosis (e.g. genetic hybridization screens for vertebrate Slit transcripts), therapy (e.g. to modulate nerve cell growth) and in the biopharmaceutical industry (e.g. as immunogens, reagents for isolating vertebrate Slit genes and polypeptides, reagents for screening chemical libraries for lead pharmacological agents, etc.).

The invention also provides methods and compositions for identifying agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the aget modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

DETAILED DESCRIPTION OF THE INVENTION

The subject methods include screens for agents which modulate Robo:ligand interactions and methods for modulating Robo:ligand interactions. Robo activation is found to regulate a wide variety of cell functions, including cell-cell interactions, cell mobility, morphology, etc. Slit polypeptides are disclosed as specific activators and inactivators of Robo polypeptides. Accordingly, the invention provides methods for modulating targeted cell function comprising the step of modulating Robo activation by contacting the cell with a modulator of a Robo:Slit interaction.

The targeted Robo polypeptide is generally naturally expressed on the targeted cells. The nucleotide sequences of exemplary natural cDNAs encoding drosophila 1, drosophila 2, C. elegans, human 1, human 2 and mouse 1 Robo polypeptides and their translates are described in Kidd et al. (1998) Cell 92, 205–215 and U.S. Ser. No. 08/971,172. The targeted Robo polypeptides comprise at least a functional Robo domain, which domain has Robo-specific amino acid sequence and binding specificity or function. Preferred Robo domains comprise at least 8, preferably at least 16, more preferably at least 32, most preferably at least 64 consecutive residues of a natural full length Robo. In a particular embodiment, the domains comprise one or more structural/functional Robo immunoglobulin, fibronectin or cytoplasmic motif domains described herein. The subject domains provide Robo-specific antigens and/or immunogens, especially when coupled to carrier proteins. For example, peptides corresponding to Robo- and human Robo-specific domains are covalently coupled to keyhole limpet antigen (KLH) and the conjugate is emulsified in Freunds complete adjuvant. Laboratory rabbits are immunized according to conventional protocol and bled. The presence of Robo-specific antibodies is assayed by solid phase immunosorbant assays using immobilized Robo polypeptides. Generic Robo-specific peptides are readily apparent as conserved regions in aligned Robo polypeptide sequences. In addition, species-specific antigenic and/or immunogenic peptides are readily apparent as diverged extracellular or cytosolic regions in alignments Human Robo-specific antibodies are characterized as uncross-reactive with non-human Robo polypeptides.

The subject domains provide Robo domain specific activity or function, such as Robo-specific cell, especially neuron modulating or modulating inhibitory activity, Robo-ligand-binding or binding inhibitory activity. Robo-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Robo regulating protein or other regulator that directly modulates Robo activity or its localization; or non-natural binding target such as a specific immune protein such as an antibody, or a Robo specific agent such as those identified in screening assays such as described below. Robo-binding specificity may be assayed by binding equilibrium constants (usually at least about $10^7 \, M^{-1}$, preferably at least about $10^8 \, M^{-1}$, more preferably at least about $10^9 \, M^{-1}$), by the ability of the subject polypeptide to function as negative mutants in Robo-expressing cells, to elicit Robo specific antibody in a heterologous host (e.g a rodent or rabbit), etc.

Similarly, the Slit polypeptide is conveniently selected from Slit polypeptides which specifically activate or inhibit the activation of the Robo polypeptide. Exemplary suitable Slit polypeptides (a) comprises a vertebrate Slit sequence disclosed herein, especially human Slit-1 (SEQ ID NO:02), or a deletion mutant thereof which specifically modulates Robo expression or a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural drosophila Slit sequence, preferably other than a natural invertebrate Slit sequence, and/or (b) is encoded by a nucleic acid comprising a natural Slit encoding sequence (such as a natural human Slit-1 encoding sequence, SEQ ID NO:01) or a fragment thereof at least 36, preferably at least 72, more preferably at least 144, most preferably at least 288 nucleotides in length which specifically hybridizes thereto. Suitable deletion mutants are readily screened in Robo binding or activation assays as described herein. Preferred Slit domains/deletion mutants/fragments comprise at least 8, preferably at least 16, more preferably at least 32, most preferably at least 64 consecutive residues of a disclosed vertebrate Slit sequences and provide a Slit specific activity, such as Slit-specific antigenicity and/or immunogenicity, especially when coupled to carrier proteins as described above for Robo above. Suitable natural Slit encoding sequence fragments are of length sufficient to encode such Slit domains. In a particular embodiment, the Slit fragments comprise species specific fragments; such fragments are readily discerned from alignments of the disclosed sequences, see, e.g. shown as unboxed sequences in Tables 1 and 2. Exemplary such human Slit-1 immunogenic and/or antigenic peptides are shown in Table 3.

TABLE 1

Alignment of human Slit-1 (SEQ ID NO:02), human Slit-2 (SEQ ID NOS:03–06), Drosophila Slit-1 (SEQ ID NO:07), C. elegans Slit-1 (SEQ ID NOS:08–09), mouse Slit-2 (SEQ ID NOS:10–11) and mouse Slit-1 (SEQ ID NOS:12–14).

```
  1  M A A P S R T T L M P P P F R L Q L R L - L I L P I L L L R H D A V H A E P Y  D-Slit
  1  M R G V G W Q - - - - - - - M L S L S L G L V L A I L - - - - - - - - - - - -  H-Slit1

40  S G G F G S S A V S S G G L G S V G I H I P G G G V G V I T E A R C P R V C S C  D-Slit
 21  - - - - - - - - - - - - - - - - - - - - - - - - - N K V A P Q A C P A Q C S C  H-Slit1

80  T G L N V D C S H R G L T S V P R K I S A D V E R L E L Q G N N L T V I Y E T D  D-Slit
 35  S G S T V D C H G L A L R S V P R N I P R N T E R L D L N G N N I T R I T K T D  H-Slit1

120  F Q R L T K L R M L Q L T D N Q I H T I E R N S F Q D L V S L E R L - - - - - -  D-Slit
 75  F A G L R H L R V L Q L M E N K I S T I E R G A F Q D L K E L E R L R L N R N H  H-Slit1
  1  - - - - - H L R V L Q L M E N R I S T I E R G A F Q D L K E L E R L R L N R N N  M-Slit1

154  - - - - - - - - - - - - - - - D I S N N V I T T V G R V F K G A Q S L R  D-Slit
115  L Q L F P E L L F L G T A K L Y R L D L S E N Q I Q A I P R K A F R G A V D I K  H-Slit1
 36  L Q L F P E L L F L G T A R L Y R L D L S E N Q I Q A I P R K A F R G A V D I K  M-Slit1

176  S L Q L D N Q I T C L D E H A F K G L V E L E I L T L N N N L T S L P H N I  D-Slit
155  N L Q L D Y N Q I S C I E D G A F R A L R D L E V L T L N N N I T R L S V A S  H-Slit1
 76  N L Q L D Y N Q I S C I E D G A F R A L R D L E V L T L N N N I T R L S V A S  M-Slit1

216  F G G L G R L R A L R L S D N P F A C D C H L S W L S R F L R S A T R L A P Y T  D-Slit
195  F N H M P K L R T F R L H S N N L Y C D C H L A W L S D W L R K P R V G L Y T  H-Slit1
116  F N H M P K L R T F R L H S N N L Y C                                          M-Slit1

256  R C Q S P S Q L K G Q N V A D L H D Q E F K C S G L T E - H A P M - - - E C G A  D-Slit
235  Q C M G P S H L R G H N V A E V Q K R E F V C S D E E G H Q S F M A P S C S V  H-Slit1

292  E N S C P H P C R C A D G I V D C R E K S L T S V P V T L P D D T T D V R L E Q  D-Slit
275  L H - C P A A C T C S N N I V D C R G K G L T E I P T N L P E T I T E I R L E Q  H-Slit1
  1  - - - - - S P C T C S N N I V D C R G K G L M E I P A N L P E G I V E I R L E Q  H-Slit2

332  N F I T E L P P K S F S S F R R L R R I D L S N N N I S R I A H D A L S G L K Q  D-Slit
314  N T I K V I P P G A F S P Y K K L R R I D L S N N Q I S E L A P D A F Q G L R S  H-Slit1
 36  N S I K A I P A G A F T Q Y K K L K R I D I S K N O I S D I A P D A F Q G L K S  H-Slit2

372  L T T L V L Y G N K I K D L P S G V F K G L G S L R L L L N A N E I S C I R K  D-Slit
354  L N S L V L Y G N K I T E L P K S L F E G L F S L Q L L L L N A N K I N C L R V  H-Slit1
 76  L T S L V L Y G N K I T E I A K G L F D G L V S L Q L L L L                      H-Slit2

1                                                                              R  D-Slit
412  D A F R D L H S L S L L S L Y D N N I Q S L A N G T F D A M K S M K T V H L A K  H-Slit1
394  D A F Q D L H N L N L L S L Y D N K L Q T I A K G T F S P L R A I Q T M H L A Q  H-Slit2

2  N P X I C D C N L Q W L A Q I N L Q K N I E T S G A R C E Q P K R L R K K K F A  CE-Slit
452  N P F I C D C N L R W L A D Y L H K N P I E T S G A R C E S P K R M H R R R I E  D-Slit
434  N P F I C D C H L K W L A D Y L H T N P I E T S G A R C T S P R R L A N K R I G  H-Slit1

42  T L P P N K F K C K G S E S F V S M Y A D S C F I D S I C P T Q C D C Y G T T V  CE-Slit
492  S L R E E K F K C S - W G E L R M K L S G E C R M D S D C P A M C H C E G T T V  D-Slit
474  Q I K S K K F R C S G T E D Y R S K L S G D C F A D L A C P E K C R C E G T T V  H-Slit1

82  D C N K R G L N T I P T S I P R F A T Q L L L S G N N I S T V D L N S N I H V L  CE-Slit
531  D C T G R R L K E I P R D I P L H T T E L L L N D N E L G R I S S D G L F G R L  D-Slit
514  D C S N Q K L N K I P E H I P Q Y T A E L R L N N N E F T V L E A T G I F K K L  H-Slit1

122  E N L E X L D L S N N H I T F I N D K S F E K L S K L R E L X L N D - - - - - -  CE-Slit
571  P H L V K L E L K R N Q L T G I E P N A F E G A S H I Q E L Q L G E N K I K E I  D-Slit
554  P Q L R K I N F S N N K I T D I E E G A F E G A S G V N E I L L T S N R L E N V  H-Slit1
  1  - - - - - - - - - - - - - - - E G A F N G A A S V Q E L M L T G N Q L E T V  H-Slit2
```

TABLE 1-continued

Alignment of human Slit-1 (SEQ ID NO:02), human Slit-2 (SEQ ID NOS:03–06), Drosophila Slit-1 (SEQ ID NO:07), C. elegans Slit-1 (SEQ ID NOS:08–09), mouse Slit-2 (SEQ ID NOS:10–11) and mouse Slit-1 (SEQ ID NOS:12–14).

```
611   S N K M F - - - - - - - - - - - - - - - - - - - - - - L G L H Q L K T L N   D-Slit
594   Q H K M F K G - L E S L K T L M L R S N R I T C V G N D S F I G L S S V R L L S   H-Slit1
 24   H G R G F R G G L S G L K T L M L R S N L I G C V S N D T F A G L S S V R L L S   H-Slit2

626   L Y D N Q I S C V M P G S F E H L N S L T S L N L A S N P F N C N C H L A W - F   D-Slit
633   L Y D N Q I T T V A P G A F D T L H S L S T L N L L A N P F N C N C Y L A W - L   H-Slit1
 64   L Y D N R I T T I T P G A F T T L V S L S T I N L L S N P F N C N C H L G A G L   H-Slit2

665   A E C V R K K S L N G G A A R C G A P S K V R D V Q I K D L P H S E F K C S S E   D-Slit
672   G E W L R K K R I V T G N P R C Q K P Y F L K E I P I Q D V A I Q D F T C D D G   H-Slit1
104   G K W L R K R R I V S G N P R C Q K P F F L K E I P I Q G V G H P G I             H-Slit2

1                                         S N K N L T S F P S R I P F D             CE-slit
705   N S E - G C L G D G Y C P P S C T C T G T V V A C S R N Q L K E I P R G I P A E   D-Slit
712   N D D N S C S P L S R C P T E C T C L D T V V R C S N K G L K V L P K G I P R D   H-Slit1

16   T T E L Y L D A N Y I N E I P A H D L N R L Y S L T K L D L S H N R L I S L E N   CE-slit
744   T S E L Y L E S N E I E Q I H Y E R I R H L R S L T R L D L S N N Q I T I L S N   D-Slit
752   V T E L Y L D G N Q F T L V P K E - L S N Y K H L T L I D L S N N R I S T L S N   H-Slit1

56   N T F S N L T R L S T L I I S Y N K L R C L Q P L A F N G L N A L R I L S L H G   CE-slit
784   Y T F A N L T K L S T L I I S Y N K L Q C L Q R H A L S G L N N L R V V S L H G   D-Slit
791   Q S F S N M T Q L L T L I L S Y N R L R C I P P R T F D G L K S L R L L S L H G   H-Slit1

96   N D I S F L P Q S A F S N L T S I T H I A V G S N S L Y C D C N M A W F S K W I   CE-slit
824   N R I S M L P E G S F E D L K S L T H I A L G S N P L Y C D C G L K W F S D W I   D-Slit
831   N D I S V V P E G A F N D L S A L S H L A I G A N P L Y C D C N M Q W L S D W V   H-Slit1

136   K S K F I E A G I A R C E Y P N T V S N Q L L L T A Q P Y Q F T C D S K V P T K   CE-slit
864   K L D Y V E P G I A R C A E P E Q M K D K L I L S T P S S S F V C R G R V R N D   D-Slit
871   K S E Y K E P G I A R C A G P G E M A D K L L L T T P S K K F T C Q G P V D V N   H-Slit1

176   L A T K C D L C L N S P C K N N A I C E T T S S R K Y T C N C T P G F Y G V H C   CE-slit
904   I L A K C N A C F E Q P C Q N Q A Q C V A L P Q R E Y Q C L C Q P G Y H G K H C   D-Slit
911   I L A K C N P C L N N P C K N D G T C N S D P V D F Y R C T C P Y G F K G Q D C   H-Slit1

216   E N Q I D A C Y G S P C L N N A T C K V - - A Q A G R F N C Y C N K G F E G D Y   CE-slit
944   E F M I D A C Y G N P C R N N A T C T V - - L E E G R F S C Q C A P G Y T G A R   D-Slit
951   D V P I H A C I S N P C K H G G T C H L K E G E E D G F W C I C A D G F E G E N   H-Slit1

254   C E K N I D D C V N S - K C E N G G K C V D L V R F C S E E L K N F Q S F Q I N   CE-slit
982   C E T N I D D C L G E I K C Q N N A T C I D - - - - - - - - - - - - - - G V E   D-Slit
991   C E V N V D D C - E D N D C E N N S T C V D - - - - - - - - - - - - - - G I N   H-Slit1

293   S Y R C D C P M E Y E G K H C E D K L E Y C T K K L N P C E N G K C I P I N G    CE-slit
1007  S Y K C E C Q P G F S G E F C D T K I Q F C S P E F N P C A N G A K C M D H F T   D-Slit
1015  N Y T C L C P P E Y T G E L C E E K L D F C A Q D L N P C Q H D S K C I L T P K   H-Slit1
                                                                  D P L P V          M-Slit2

333   S Y S C M C S P G F T G N N C E T N I D D C K N V E C Q N G G S C V D G I L S Y  CE-slit
1047  H Y S C D C Q A G F H G T N C T D N I D D C Q N H M C Q N G G T C V D G I N D Y  D-Slit
1055  G F K C D C T P G Y V G E H C D I D F D D C Q D N K C K N G A H C T D A V N G Y  H-Slit1
  1   - - - - - - - - - - - - - - N N D D C V G H K C R H G A Q C V D E V N G Y      M-Slit1
  1   W P R C E C M P G Y A G D N C S E N Q D D C R D H R C Q N G A Q C M D E V N S Y  H-Slit2
  6   H H R C E C M L G Y T G D N C S E N Q D D C K D H K C Q N G A Q C V D E V N S Y  M-Slit2

373   D C L C R P G Y A G Q Y C E I P P M M D M E Y Q K T D A C Q Q S A C G Q G - E C   CE-slit
1087  Q C R C P D D Y T G K Y C E G H N M I S M M Y P Q T S P C Q N H E C K H G V - C   D-Slit
1095  T C I C P E G Y S G L F C E F S P - - P M V L P R T S P C D N F D C Q N G A Q C   H-Slit1
 24   T C I C P Q G F S G L F C E H P P - - P M V L L Q T S P C D Q Y E C Q N G A Q C   M-Slit1
 41   S C L C A E G Y S G Q L C E I P P - - H L P A P K - S P C E G T E C Q N G A N C   H-Slit2
 46   A C L C V E G Y S G Q L C E I P P - - - - - A P R - S S C E G T E C Q N G A N C   M-Slit2
```

TABLE 1-continued

Alignment of human Slit-1 (SEQ ID NO:02), human Slit-2 (SEQ ID NOS:03–06), Drosophila
Slit-1 (SEQ ID NO:07), C. elegans Slit-1 (SEQ ID NOS:08–09), mouse Slit-2 (SEQ ID NOS:10–
11) and mouse Slit-1 (SEQ ID NOS:12–14).

```
412   V A S Q N - S S D F T C K C H E G F S G P S C D R Q M S V G F K N P G A Y L A L CE-Slit
1126  F Q P N A Q G S D Y L C R C H P G Y T G K W C E Y L T S I S F V H N N S F V E L D-Slit
1133  I V R I N E P - - - I C Q C L P G Y Q G E K C E K L V S V N F I N K E S Y L Q I H-Slit1
62    I V V Q Q E P - - - T C R C P P G F A G P R C E K L I T V N F V G K D S Y V E L M-Slit1
78    V D Q G N R P - - - V C Q C L P G F G G P E C E K L L S V N F V D R D T Y L Q F H-Slit2
80    V D Q G S R P - - - V C Q C L P G F G G P E C E K L L S V N F V D R D T Y L Q F M-Slit2

451   D P L A S - - D G T I T M T L R T T S K I G I L L Y G D D H F V S A E L Y D G CE-Slit
1166  E P L R T R P E A N V T I V F S S A E Q N G I L M Y D G Q D A H L A V E L F N G D-Slit
1170  P S A K V R P Q T N I T L Q I A T D E D S G I L L Y G D K D H I A V E L Y R G H-Slit1
99    A S A K V R                                                                    M-Slit1
115   T D L Q N W X R X N I T L Q V F T A E D N G I L L Y N G G N D H I A V X L Y X G H-Slit2
117   T D L Q N W P R A N I T L Q V S T A E D N G I L L Y N G D N D H I A V E L Y   M-Slit2

489   R V K L V Y Y I G N F P A S H M Y S S V K V N D G L P H R I S I R T S E R K C F CE-Slit
1206  R I R V S Y D V G N H P V S T M Y S F E M V A D G K Y H A V E L L A I K K N F T D-Slit
1210  R V R A S Y D T G S H P A S A I Y S V E T I N D G N F H I V E L L A L D Q S L S H-Slit1
155   H V R F S Y                                                                     H-Slit2

529   L Q I D K N P V Q I V E N S G K S D Q L I T K G K E M L Y I G G L P I E K S Q D CE-Slit
1246  L R V D R G L A R S I I N E G S N D Y L - - K L T T P M F L G G L P V D P A Q Q D-Slit
1250  L S V D G G N P K I I T N L S K Q S T L - - N F D S P L Y V G G M P G K S N V A H-Slit1
1     I L - - - - - - - - - - - - - - - - - - - - - - - - - - - - - - - - - D V A M-Slit1

569   A K R F H V K N S E S L K G C I S S I T I N E V P I N L Q Q A L E N V N T E Q CE-Slit
1284  A Y K N W Q I R N L T S F K G C M K E V W I N H K L V D F G N A Q R Q K I T P D-Slit
1288  S L R Q A P G Q N G T S F H G C I R N L Y I N S E L Q D F Q K V P M Q T G I L P H-Slit1
6     S L R Q A P G E N G T S F H G C I R N L Y I N S E L Q D F R K M P M Q T G I L P M-Slit1

609   S C - - - - - - - - - - - - - S A T V N F - - - - - - - - - - - - - - - CE-Slit
1324  G C A L - - - - L E G E Q Q E E E D D E Q D F M D E - - - - - - T P H I K E E P D-Slit
1328  G C E P C H K K V C A H G T C Q P S S Q A G F T C E C Q E G W M G P L C D Q R T H-Slit1
46    G C E P C H K K V C A H G C C Q P S S Q S G F T C E C E E G W M G P L C D Q R T M-Slit1

617   - - - C A G I D C G N G - K C T N N A L S R K G Y M C Q C D S H F S G E H C D E CE-Slit
1354  V D P C L E N K C R R G S R C V P N S N A R D G Y Q C K C K H G Q R G R Y C D Q D-Slit
1368  N D P C L G N K C V H G T - C L P I N A F - - S Y S C K C L E G H G G V L C D E H-Slit1
86    N D P C L G N K C V H G T - C L P I N A F - - S Y S C K C L E G H G G V L C D E M-Slit1

653   - - - - - - - - - - - - - - - - - - - - - - - - - - - - - - - - - - - - - CE-Slit
1394  G E G S T E P - - - - - - - - - - - - - - - - - - - - - - - P T V T A A S - - D-Slit
1405  E E D L F N P C Q A I K C K H G K C R L S G L G Q P Y C E C S G Y T G D S C D H-Slit1
123   E E D L F N P C Q M I K C K H G K C R L S G V G Q P Y C E C N S G F T G D S C D M-Slit1
1     - - - - - - - - - - - - Q C H I S D Q G E P Y C L C Q P G F S G E H C Q H-Slit2
1     - - - - - - - - - - A F K C H H G Q C H I S D R G E P Y C L C Q P G F S G H H C E M-Slit2

655   K R I K C D K Q K F R R H H I E N E - - - - C R S V D R I K I A E C N G Y C G G CE-Slit
1405  T - - - C R K E Q V R E Y Y T E N D - - - - C R S R Q P L K Y A K C V G G C G - D-Slit
1445  R E I S C R G E R I R D Y Y Q K Q Q G Y A A C Q T T K V S R L E C R G G C A G H-Slit1
163   R E I S C R G E R I R D Y Y Q K Q Q G Y A A C Q T T K V S R L E C R G G C A G M-Slit1
25    Q E N P C L G Q V V R E V I R R Q K G Y A S C A T A S K V P I M E C R G G C - G H-Slit2
32    Q E N P C M G E I V R E A I R R Q K D Y A S C A T A S K V P I M E C R G G C - G M-Slit2

689   E Q N C C T A V K K K Q R K V K M I C K N G T T K I S T V H I I R Q C Q C E P T CE-Slit
1440  - N Q C C A A K I V R R R K V R M V C S N N R K Y I K N L D I V R K C G C - - T D-Slit
1485  G Q - C C G P L R S K R R K Y S F E C T D G S S F V D E V E K V V K C G C T R - H-Slit1
203   G Q - C C G P L R S K R R K Y S F E C T D G S S F V D E V E K V V K C G C A R - M-Slit1
64    P Q - C C Q P T R S K R R K Y V F Q C T D G S S F V E E V E R H L E C G C L A - H-Slit2
71    T T - C C Q P I R S K R R K Y V F Q C T D G S S F V E E V E R H L E C G C R A - M-Slit2

729   K S V L - - S E K                                                              CE-Slit
1477  K K C Y                                                                        D-Slit
1523  - - - - C V S                                                                  H-Slit1
241   - - - - C A S                                                                  M-Slit1
102   - - - - C - S                                                                  H-Slit2
109   - - - - C - S                                                                  M-Slit2
```

TABLE 2

Alignment of human Slit-1 (SEQ ID NO:02) and Drosophila Slit-1 (SEQ ID NO:07)

```
1    M A A P S R T T L M P P P F R L Q L R L - L I L P I L L L R H D A V H A E P Y  D-Slit
1    M R G V G W Q - - - - - - - M L S L S L G L V L A I L - - - - - - - - - - - -  H-Slit1

40   S G G F G S S A V S S G G L G S V G I H I P G G G V G V I T E A R C P R V C S C  D-Slit
21   - - - - - - - - - - - - - - - - - - - - - - - - N K V A P Q A C P A Q C S C  H-Slit1

80   T G L N V D C S H R G L T S V P R K I S A D V E R E L Q G N N L T V I Y E T D  D-Slit
35   S G S T V D C H G L A L R S V P R N I P R N T E R L D L N G N N I T R I T K T D  H-Slit1

120  F Q R L T K L R M L Q L T D N Q I H T I E R N S F Q D L V S L E R L - - - - - -  D-Slit
75   F A G L R H L R V L Q L M E N K I S T I E R G A F Q D L K E L E R L R L N R N H  H-Slit1

154  - - - - - - - - - - - - - - - - - D I S N N V I T T V G R V F K G A Q S L R D  D-Slit
115  L Q L F P E L L F L G T A K L Y R L D L S E N Q I Q A I P R K A F R G A V D I K  H-Slit1

176  S L Q L D N N Q I T C L D E H A F K G L V E L E I L T L N N N L T S L P H N I D  D-Slit
155  N L Q L D Y N Q I S C I E D G A F R A L R D L E V L T L N N N I T R L S V A S  H-Slit1

216  F G G L G R L R A L R L S D N P F A C D C H L S W L S R F L R S A T R L A P Y T  D-Slit
195  F N H M P K L R T F R L H S N N L Y C D C H L A W L S D W L R K R P R V G L Y T  H-Slit1

256  R C Q S P S Q L K G Q N V A D L H D Q E F K C S G L T E - H A P M - - - E C G A  D-Slit
235  Q C M G P S H L R G H N V A E V Q K R E F V C S D E E G H Q S F M A P S C S V  H-Slit1

292  E N S C P H P C R C A D G I V D C R E K S L T S V P V T L P D D T T D V R L E Q  D-Slit
275  L H - C P A A C T C S N N I V D C R G K G L T E I P T N L P E T I T E I R L E Q  H-Slit1

332  N F I T E L P P K S F S S F R R L R R I D L S N N N I S R I A H D A L S G L K Q  D-Slit
314  N T I K V I P P G A F S P Y K K L R R I D L S N N Q I S E L A P D A F Q G L R S  H-Slit1

372  L T T L V L Y G N K I K D L P S G V F K G L G S L R L L L N A N E I S C I R K  D-Slit
354  L N S L V L Y G N K I T E L P K S L F E G L F S L Q L L L L N A N K I N C L R V  H-Slit1

412  D A F R D L H S L S L L S L Y D N N I Q S L A N G T F D A M K S M K T V H L A K  D-Slit
394  A A F Q D L H N L N L L S L Y D N K L Q T I A K G T F S P L R A I Q T M H L A Q  H-Slit1

452  N P F I C D C N L R W L A D Y L H K N P I E T S G A R C E S P K R M H R R I E  D-Slit
434  N P F I C D C H L K W L A D Y L H T N P I E T S G A R C T S P R R L A N K R I G  H-Slit1

492  S L R E E K F K C S - W G E L R M K L S G E C R M D S D C P A M C H C E G T T V  D-Slit
474  Q I K S K K F R C S G T E D Y R S K L S G D C F A D L A C P E K C R C E G T T V  H-Slit1

531  D C T G R R L K E I P R D I P L H T T E L L L N D N E L G R I S S D G L F G R L  D-Slit
514  D C S N Q K L N K I P E H I P Q Y T A E L R L N N N E F T V L E A T G I F K K L  H-Slit1

571  P H L V K L E L K R N Q L T G I E P N A F E G A S H I Q E L Q L G E N K I K E I D  D-Slit
554  P Q L R K I N F S N N K I T D I E E G A F E G A S G V N E I L L T S N R L E N V  H-Slit1

611  S N K M F L G L H Q L K T L - - - - - - - - - - - - - - - - - - - - - N L D-Slit
594  Q H K M F K G L E S L K T L M L R S N R I T C V G N D S F I G L S S V R L L S L  H-Slit1

627  Y D N Q I S C V M P G S F E H L N S L T S L N L A S N P F N C N H L A W F A E  D-Slit
634  Y D N Q I T T V A P G A F D T L H S L S T L N L L A N P F N C N C Y L A W L G E  H-Slit1

667  C V R K K S L N G G A A R C G A P S K V R D V Q I K D L P H S E F K C S S E N S  D-Slit
674  W L R K K R I V T G N P R C Q K P Y F L K E I P I Q D V A I Q D F T C D D G N D  H-Slit1

707  E - G C L G D G Y C P P S C T C T G T V V A C S R N Q L K V I P R G I P A E T S  D-Slit
714  D N S C S P L S R C P T E C T C L D T V V R C S N K G L K E L P K G I P R D V T  H-Slit1
```

TABLE 2-continued

Alignment of human Slit-1 (SEQ ID NO:02) and Drosophila Slit-1 (SEQ ID NO:07)

```
746  E L Y L E S N E I E Q I H Y E R I R H L R S L T R L D L S N N Q I T I L S N Y T  D-Slit
754  E L Y L D G N Q F T L V P K E - L S N Y K H L T L I D L S N N R I S T L S N Q S  H-Slit1

786  F A N L T K L S T L I I S Y N K L Q C L Q R H A L S G L N N L R V V S L H G N R  D-Slit
793  F S N M T Q L L T L I L S Y N R L R C I P P R T F D G L K S L R L L S L H G N D  H-Slit1

826  I S M L P E G S F E D L K S L T H I A L G S N P L Y C D C G L K W F S D W I K L  D-Slit
833  I S V V P E G A F N D L S A L S H L A I G A N P L Y C D C N M Q W L S D W V K S  H-Slit1

866  D Y V E P G I A R C A E P E Q M K D K L I L S T P S S S F V C R G R V R N D I L  D-Slit
873  E Y K E P G I A R C A G P G E M A D K L L L T T P S K K F T C Q G P V D V N I L  H-Slit1

906  A K C N A C F E Q P C Q N Q A Q C V A L P Q R E Y Q C L C Q P G Y H G K H C E F  D-Slit
913  A K C N P C L S N P C K N D G T C N S D P V D F Y R C T C P Y G F K G Q D C D V  H-Slit1

946  M I D A C Y G N P C R N N A T C T V L E - - E G R F S C Q C A P G Y T G A R C E  D-Slit
953  P I H A C I S N P C K H G G T C H L K E G E E D G F W C I C A D G F E G E N C E  H-Slit1

984  T N I D D C L G E I K C Q N N A T C I D G V E S Y K C E C Q P G F S G E F C D T  D-Slit
993  V N V D D C - E D N D C E N N S T C V D G I N N Y T C L C P P E Y T G E L C E E  H-Slit1

1024 K I Q F C S P E F N P C A N G A K C M D H F T H Y S C D C Q A G F H G T N C T D  D-Slit
1032 K L D F C A Q D L N P C Q H D S K C I L T P K G F K C D C T P G Y V G E H C D I  H-Slit1

1064 N I D D C Q N H M C Q N G G T C V D G I N D Y Q C R C P D D Y T G K Y C E G H N  D-Slit
1072 D F D D C Q D N K C K N G A H C T D A V N G Y T C I C P E G Y S G L F C E F S P  H-Slit1

1104 M I S M M Y P Q T S P C Q N H E C K H G V - C F Q P N A Q G S D Y L C R C H P G  D-Slit
1112 - - P M V L P R T S P C D N F D C Q N G A Q C I - - - V R I N E P I C Q C L P G  H-Slit1

1143 Y T G K W C E Y L T S I S F V H N N S F V E L E P L R T R P E A N V T I V F S S  D-Slit
1147 Y Q G E K C E K L V S V N F I N K E S Y L Q I P S A K V R P Q T N I T L Q I A T  H-Slit1

1183 A E Q N G I L M Y D G Q D A H L A V E L F N G R I R V S Y D V G N H P V S T M Y  D-Slit
1187 D E D S G I L L Y K G D K D H I A V E L Y R G R V R A S Y D T G S H P A S A I Y  H-Slit1

1223 S F E M V A D G K Y H A V E L L A I K K N F T L R V D R G L A R S I I N E G S N  D-Slit
1227 S V E T I N D G N F H I V E L L A L D Q S L S L S V D G G N P K I I T N L S K Q  H-Slit1

1263 D Y L K L T T P M F L G G L P V D P A Q Q A Y K N W Q I R N L T S F K G C M K E  D-Slit
1267 S L L N F D S P L Y V G G M P G K S N V A S L R Q A P G Q N G T S F H G C I R N  H-Slit1

1303 V W I N H K L V D F G N A Q R Q Q K I T P G C A L - - - - L E G E Q Q E E D D  D-Slit
1307 L Y I N S E L Q D F Q K V P M Q T G I L P G C E P C H K K V C A H G T C Q P S S  H-Slit1

1339 E Q D F M D E - - - - - - T P H I K E E P V D P C L E N K C R G S R C V P N S  D-Slit
1347 Q A G F T C E C Q E G W M G P L C D Q R T N D P C L G N K C V H G T - C L P I N  H-Slit1

1373 N A R D G Y Q C K C K H G Q R G R Y C D Q G E G S T E P - - - - - - - - - - - -  D-Slit
1386 A F - - S Y S C K C L E G H G G V L C D E E E D L F N P C Q A I K C K H G K C R  H-Slit1

1401 - - - - - - - - - - - - - P T V T A A S - - - - - T C R K E Q V R E Y Y T E N D -  D-Slit
1424 L S G L G Q P Y C E C S S G Y T G D S C D R E I S C R G E R I R D Y Y Q K Q Q G  H-Slit1

1423 - - - C R S R Q P L K Y A K C V G G C - G N Q C C A A K I V R R R K V R M V C S  D-Slit
1464 Y A A C Q T T K K V S R L E C R G G C A G G Q C C G P L R S K R R K Y S F E C T  H-Slit1

1459 N N R K Y I K N L D I V R K C G C T K K C Y                                       D-Slit
1504 D G S S F V D E V E K V V K C G C T R - C V S                                    H-Slit1
```

TABLE 3

Immunogenic human Slit-1 polypeptides eliciting Slit-1 specific rabbit polyclonal antibody: Slit polypeptide-KLH conjugates immunized per protocol described above.

| Slit Polypeptide | Immunogenicity | Slit Polypeptide | Immunogenicity |
| --- | --- | --- | --- |
| SEQ ID NO: 02, res. 1–10 | +++ | SEQ ID NO: 02, res. 561–576 | +++ |
| SEQ ID NO: 02, res. 29–41 | +++ | SEQ ID NO: 02, res. 683–697 | +++ |
| SEQ ID NO: 02, res. 75–87 | +++ | SEQ ID NO: 02, res. 768–777 | +++ |
| SEQ ID NO: 02, res. 92–109 | +++ | SEQ ID NO: 02, res. 798–813 | +++ |
| SEQ ID NO: 02, res. 132–141 | +++ | SEQ ID NO: 02, res. 882–894 | +++ |
| SEQ ID NO: 02, res. 192–205 | +++ | SEQ ID NO: 02, res. 934–946 | +++ |
| SEQ ID NO: 02, res. 258–269 | +++ | SEQ ID NO: 02, res. 1054–1067 | +++ |
| SEQ ID NO: 02, res. 295–311 | +++ | SEQ ID NO: 02, res. 1181–1192 | +++ |
| SEQ ID NO: 02, res. 316–330 | +++ | SEQ ID NO: 02, res. 1273–1299 | +++ |
| SEQ ID NO: 02, res. 373–382 | +++ | SEQ ID NO: 02, res. 1383–1397 | +++ |
| SEQ ID NO: 02, res. 403–422 | +++ | SEQ ID NO: 02, res. 1468–1477 | +++ |
| SEQ ID NO: 02, res. 474–485 | +++ | SEQ ID NO: 02, res. 1508–1517 | +++ |

The subject domains provide Slit domain specific activity or function, such as Slit-specific cell, especially neuron modulating or modulating inhibitory activity, Slit-ligand-binding or binding inhibitory activity. Slit-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Slit regulating protein or other regulator that directly modulates Slit activity or its localization; or non-natural binding target such as a specific immune protein such as an antibody, or a Slit specific agent such as those identified in screening assays such as described below. Slit-binding specificity may be assayed by binding equilibrium constants (usually at least about $10^7$ $M^{-1}$, preferably at least about $10^8$ $M^{-1}$, more preferably at least about $10^9$ $M^{-1}$), by the ability of the subject polypeptide to function as negative mutants in Slit-expressing cells, to elicit Slit specific antibody in a heterologous host (e.g a rodent or rabbit), etc.

In one embodiment, the Slit polypeptides are encoded by a nucleic acid comprising SEQ ID NO:01 or a fragment thereof which hybridizes with a full-length strand thereof, preferably under stringent conditions. Such nucleic acids comprise at least 36, preferably at least 72, more preferably at least 144 and most preferably at least 288 nucleotides of SEQ ID NO:01. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE (Conditions I); preferably hybridizing in a buffer comprising 50% formamide in 5×SSPE buffer at a temperature of 42° C. and remaining bound when subject to washing at 42° C. with 0.2×SSPE buffer at 42° C. (Conditions II). Exemplary nucleic acids which hybridize with a strand of SEQ ID NO:01 are shown in Table 4.

TABLE 4

Exemplary nucleic acids which hybridize with a strand of SEQ ID NO: 01 under Conditions I and/or II.

| Slit Nucleic Acid | Hybridization | Slit Nucleic Acid | Hybridization |
| --- | --- | --- | --- |
| SEQ ID NO: 01, nucl. 1–47 | + | SEQ ID NO: 01, nucl. 1258–1279 | + |
| SEQ ID NO: 01, nucl. 58–99 | + | SEQ ID NO: 01, nucl. 1375–1389 | + |
| SEQ ID NO: 01, nucl. 95–138 | + | SEQ ID NO: 01, nucl. 1581–1595 | + |
| SEQ ID NO: 01, nucl. 181–220 | + | SEQ ID NO: 01, nucl. 1621–1639 | + |
| SEQ ID NO: 01, nucl. 261–299 | + | SEQ ID NO: 01, nucl. 1744–1755 | + |
| SEQ ID NO: 01, nucl. 274–315 | + | SEQ ID NO: 01, nucl. 1951–1969 | + |
| SEQ ID NO: 01, nucl. 351–389 | + | SEQ ID NO: 01, nucl. 2150–2163 | + |
| SEQ ID NO: 01, nucl. 450–593 | + | SEQ ID NO: 01, nucl. 2524–2546 | + |
| SEQ ID NO: 01, nucl. 524–546 | + | SEQ ID NO: 01, nucl. 2761–2780 | + |
| SEQ ID NO: 01, nucl. 561–608 | + | SEQ ID NO: 01, nucl. 2989–2999 | + |
| SEQ ID NO: 01, nucl. 689–727 | + | SEQ ID NO: 01, nucl. 3108–3117 | + |
| SEQ ID NO: 01, nucl. 708–737 | + | SEQ ID NO: 01, nucl. 3338–3351 | + |
| SEQ ID NO: 01, nucl. 738–801 | + | SEQ ID NO: 01, nucl. 3505–3514 | + |
| SEQ ID NO: 01, nucl. 805–854 | + | SEQ ID NO: 01, nucl. 3855–3867 | + |
| SEQ ID NO: 01, nucl. 855–907 | + | SEQ ID NO: 01, nucl. 4010–4025 | + |
| SEQ ID NO: 01, nucl. 910–953 | + | SEQ ID NO: 01, nucl. 4207–4219 | + |
| SEQ ID NO: 01, nucl. 1007–1059 | + | SEQ ID NO: 01, nucl. 4333–4345 | + |
| SEQ ID NO: 01, nucl. 1147–1163 | + | SEQ ID NO: 01, nucl. 4521–4529 | + |

A wide variety of cell types express Robo polypeptides subject to regulation by the disclosed methods, including many neuronal cells, transformed cells, infected (e.g. virus) cells, etc. Ascertaining Robo binding or activation is readily effected by binding assays or cells function assays as disclosed herein or in the cited copending applications. Accordingly, indications for the subject methods encompass a wide variety of cell types and function, including axon outgrowth, tumor cell invasion or migration, etc. The target cell may reside in culture or in situ, i.e. within the natural host. For in situ applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Slit polypeptides may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic polypeptides. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts.

In one embodiment, the invention provides administering the subject Slit polypeptides in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations for polypeptide-based therapeutics are known in the art. The compositions may be provided in any convenient form including tablets, capsules, troches, powders, sprays, creams, etc. As such the compositions, in pharmaceutically acceptable dosage units or in bulk, may be incorporated into a wide variety of containers. For example, dosage units may be included in a variety of containers including capsules, pills, etc. The compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics,* 9th Ed., 1996, McGraw-Hill.

In another aspect, the invention provides methods of screening for agents which modulate Robo-Slit interactions. These methods generally involve forming a mixture of a Robo-expressing cell, a Slit polypeptide and a candidate agent, and determining the effect of the agent on the amount of Robo expressed by the cell. The methods are amenable to automated, cost-effective high throughput screening of chemical libraries for lead compounds. Identified reagents find use in the pharmaceutical industries for animal and human trials; for example, the reagents may be derivatized and rescreened in vitro and in vivo assays to optimize activity and minimize toxicity for pharmaceutical development. Cell and animal based neural guidance/repulsion assays are described in detail in the experimental section below.

The amino acid sequences of the disclosed vertebrate Slit polypeptides are used to back-translate Slit polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural Slit-encoding nucleic acid sequences ("GCG" software, Genetics Computer Group, Inc, Madison Wis.). Slit-encoding nucleic acids used in Slit-expression vectors and incorporated into recombinant host cells, e.g. for expression and screening, transgenic animals, e.g. for functional studies such as the efficacy of candidate drugs for disease associated with Slit-modulated cell function, etc.

The invention also provides nucleic acid hybridization probes and replication/amplifaction primers having a vertebrate Slit cDNA specific sequence comprising a fragment of a disclosed vertebrate cDNA sequence, and sufficient to effect specific hybridization thereto. Such primers or probes are at least 12, preferably at least 24, more preferably at least 36 and most preferably at least 96 nucleotides in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Slit nucleic acids can also be distinguished using alignment algorithms, such as BLASTX (Altschul et al. (1990) Basic Local Alignment Search Tool, J Mol Biol 215, 403–410). In addition, the invention provides nucleic acids having a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural drosophila Slit sequence, preferably other than a natural invertebrate Slit sequence. In a particular embodiment, the Slit polynucleotide fragments comprise species specific fragments; such fragments are readily discerned from alignments of the disclosed sequences.

The subject nucleic acids are of synthetic/non-natural sequences and/or are recombinant, meaning they comprise a non-natural sequence or a natural sequence joined to nucleotide(s) other than that which it is joined to on a natural chromosome. The subject recombinant nucleic acids comprising the nucleotide sequence of disclosed vertebrate Slit nucleic acids, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bp, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of Slit genes and gene transcripts and in detecting or amplifying nucleic acids encoding additional Slit homologs and structural analogs. In diagnosis, Slit hybridization probes find use in identifying wild-type and mutant Slit alleles in clinical and laboratory samples. Mutant alleles are used to generate allele-specific oligonucleotide (ASO) probes for high-throughput clinical diagnoses. In therapy, therapeutic Slit nucleic acids are used to modulate cellular expression or intracellular concentration or availability of active Slit. Exemplary human Slit-1 probes and primers are shown in Table 5 and Table 6.

TABLE 5

Hybridization Probes for Regions of Human Slit-1.

| | |
|---|---|
| Hybridization probe for first leucine rich repeat region | SEQ ID NO: 01, nucleotides 82–828 |
| Hybridization probe for second leucine rich repeat region | SEQ ID NO: 01, nucleotides 829–1503 |
| Hybridization probe for third leucine rich repeat region | SEQ ID NO: 01, nucleotides 1504–2166 |
| Hybridization probe for fourth leucine rich repeat region | SEQ ID NO: 01, nucleotides 2167–2751 |
| Hybridization probe for EGF repeats one to five | SEQ ID NO: 01, nucleotides 2752–3327 |
| Hybridization probe for the sixth EGF repeat and preceding spacer region | SEQ ID NO: 01, nucleotides 3328–3461 |
| Hybridization probe for the 99aa spacer/G-loop region | SEQ ID NO: 01, nucleotides 3462–3987 |
| Hybridization probe for EGF repeats seven to nine | SEQ ID NO: 01, nucleotides 3988–4341 |
| Hybridization probe for the cysteine knot region | SEQ ID NO: 01, nucleotides 4342–4575 |

TABLE 6

PCR Primers for regions of Human Slit.

| | |
|---|---|
| PCR Primers for first leucine rich repeat region | Forward: SEQ ID NO: 01, nucleotides 82–111 Reverse: reverse complement of SEQ ID NO: 01, nucleotides 799–828 |
| PCR Primers for second leucine rich repeat region | Forward: SEQ ID NO: 01, nucleotides 829–858 Reverse: reverse complement of SEQ ID NO: 01, nucleotides 1474–1503 |
| PCR Primers for third leucine rich repeat region | Forward: SEQ ID NO: 01, nucleotides 1504–1533 Reverse: reverse complement of SEQ ID NO: 01, nucleotides 2137–2166 |
| PCR Primers for fourth leucine rich repeat region | Forward: SEQ ID NO: 01, nucleotides 2167–2196 Reverse: reverse complement of SEQ ID NO: 01, nucleotides 2722–2751 |
| PCR Primers for EGF repeats one to five | Forward: SEQ ID NO: 01, nucleotides 2752–2781 Reverse: reverse complement of SEQ ID NO: 01, nucleotides 3298–3327 |
| PCR Primers for the sixth EGF repeat and preceding spacer region | Forward: SEQ ID NO: 01, nucleotides 3328–3357 Reverse: reverse complement of SEQ ID NO: 01, nucleotides 3432–3461 |
| PCR Primers for the 99aa spacer/G-loop region | Forward: SEQ ID: 01, nucleotides 3462–3491 Reverse: reverse complement of SEQ ID NO: 01, nucleotides 3958–3987 |
| PCR Primers for EGF repeats seven to nine | Forward: SEQ ID NO: 01, nucleotides 3988–4017 Reverse: reverse complement of SEQ ID NO: 01, nucleotides 4312–4341 |
| PCR Primers for the cysteine knot region | Forward: SEQ ID NO: 01, nucleotides 4342–4371 Reverse: reverse complement of SEQ ID NO: 01, nucleotides 4546–4575 |

Leucine rich repeats (LRRs) are predicted by comparison with known proteins and by the presence of a leucine rich core sequence. In slit proteins, the LRRs are flanked by conserved sequences referred to as the amino- and carboxy-flanking regions. These flanking regions are found in other known proteins, but only in a few instances are both the amino- and carboxy- flank regions present in a single protein.

The so called "99aa spacer" is actually ~200 amino acids in the Drosophila protein and 174 amino acids in Human Slit-1. This region shows homology to the G-loops of laminin A chains.

Cysteine knots are dimerisation domains defined by the presence of six cysteine residues between which disulphide bridges form. The only absolutely conserved residues are the six cysteines, and spacing between them is highly variable, apart from between cysteines 2 and 3, and 5 and 6. The glycine between cysteines 2 and 3 is only present in a subset of cysteine knots. Drosophila slit and Human slit-1 both have an extra cysteine after cysteines 5 and 6: this may serve as an intermolecular bond. Human Slit-1 gene displays the overall structure of the Drosophila gene, and amino acid conservation is found along the entire length of the protein (48% homology at the amino acid sequence excluding the signal sequence; see below). The Human gene has an extra LRR between LRR2 and LRR3 of the first set of LRRs; in the third set, the Human gene has an extra LRR between LRR3 and LRR4. The Human gene has two extra EGF repeats, on either side of the seventh EGF repeat in Drosophila slit.

Isolation of Human Slit-1

Searching of the EST database revealed an EST, ab16g10.r1, with homology to the 99aa spacer region of Drosophila slit. This EST was used to probe a Human fetal brain library (Stratagene), and clones for Human slit-1 were isolated.

| | |
|---|---|
| Features of Human Slit Predicted Protein | |
| Signal sequence | SEQ ID NO: 02, residues 7–24 |
| First amino-flanking sequence | SEQ ID NO: 02, residues 28–59 |
| First set of Leucine Rich Repeats | SEQ ID NO: 02, residues 60–179 (6 repeats) |
| First carboxy-flanking sequence | SEQ ID NO: 02, residues 180–276 |
| Second amino-flanking sequence | SEQ ID NO: 02, residues 277–308 |
| Second set of Leucine Rich Repeats | SEQ ID NO: 02, residues 309–434 (5 repeats) |
| Second carboxy-flanking sequence | SEQ ID NO: 02, residues 435–501 |
| Third amino-flanking sequence | SEQ ID NO: 02, residues 502–533 |
| Third set of Leucine Rich Repeats | SEQ ID NO: 02, residues 534–560 (5 repeats) |
| Third carboxy-flanking sequence | SEQ ID NO: 02, residues 661–722 |
| Fourth amino-flanking sequence | SEQ ID NO: 02, residues 723–754 |
| Fourth set of Leucine Rich Repeats | SEQ ID NO: 02, residues 755–855 (4 repeats) |
| Fourth carboxy-flanking sequence | SEQ ID NO: 02, residues 856–917 |
| First EGF repeat | SEQ ID NO: 02, residues 918–952 |
| Second EGF repeat | SEQ ID NO: 02, residues 953–993 |
| Third EGF repeat | SEQ ID NO: 02, residues 994–1031 |
| Fourth EGF repeat | SEQ ID NO: 02, residues 1032–1071 |
| Fifth EGF repeat | SEQ ID NO: 02, residues 1072–1109 |
| Spacer | SEQ ID NO: 02, residues 1110–1116 |
| Sixth EGF repeat | SEQ ID NO: 02, residues 1117–1153 |
| "99aa spacer" | SEQ ID NO: 02, residues 1155–1329 |
| Seventh EGF repeat | SEQ ID NO: 02, residues 1330–1366 |
| Eighth EGF repeat | SEQ ID NO: 02, residues 1367–1404 |
| Nineth EGF repeat | SEQ ID NO: 02, residues 1405–1447 |
| Cysteine knot motif | SEQ ID NO: 02, residues 1448–1525 |
| Amino acid identity between Drosophila and Human Slit-1 | |
| First amino-flanking sequence | 53% |
| First set of Leucine Rich Repeats | 52% (54%, 67%, NA, 38%, 54%, 50%) |
| First carboxy-flanking sequence | 42% |
| Second amino-flanking sequence | 50% |
| Second set of Leucine Rich Repeats | 60% (54%, 58%, 67%, 71%, 50%) |
| Second carboxy-flanking sequence | 62% |
| Third amino-flanking sequence | 56% |
| Third set of Leucine Rich Repeats | 49% (46%, 46%, 42%, NA, 58%) |
| Third carboxy-flanking sequence | 36% |
| Fourth amino-flanking sequence | 53% |

| Features of Human Slit Predicted Protein | |
|---|---|
| Fourth set of Leucine Rich Repeats | 48% (25%, 58%, 46%, 63%) |
| Fourth carboxy-flanking sequence | 63% |
| First EGF repeat | 34% |
| Second EGF repeat | 46% |
| Third EGF repeat | 46% |
| Fourth EGF repeat | 35% |
| Fifth EGF repeat | 47% |
| Spacer | 22% |
| Sixth EGF repeat | 40% |
| "99aa spacer" | 38% |
| Seventh EGF repeat | 11%/NA |
| Eighth EGF repeat | 44% |
| Nineth EGF repeat | 29%/NA |
| Cysteine knot motif | 34% |

NA: not applicable due to absence of homologous repeat.
Figures for individual LLRs are shown in brackets.

The following examplary assay is offered by way of illustration and not by way of limitation:

EXAMPLES

Protocol for Ligand Screening of Transfected COS Cells.

I. Prepare the Ligand

Expression Construct: cDNAs encoding targeted Slit polypeptides are tagged with the Fc portion of human IgG and subcloned into a 293 expression vector (pCEP4:In Vitrogen).

Transfection: 293 EBNA cells are transfected ($CaPO_4$ method) with the Slit expression constructs. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Prepare Truncated Receptor (Positive Control)

Expression Construct: cDNA encoding a corresponding Robo C-terminal deletion mutant comprising the extracellular domain (truncated immediately N-terminal to the transmembrane region) is subcloned into a 293 expression vector (pCEP4:In Vitrogen).

Transfection: 293 EBNA cells are transfected ($CaPO_4$ method) with the receptor mutant expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Transfect COS Cells

Seed COS cells (250,000) on 35 mm dishes in 2 ml DME/10% FCS.

18–24 h later, dilute 1 ug of Robo-encoding DNA (cDNA cloned into pMT21 expression vector) into 200 ul serum-free media and add 6 ul of Lipofectamine (Gibco). Incubate this solution at room temperature for 15–45 min.

Wash the cells 2×with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

III. Ligand Binding Assay

Wash plates of transfected COS cells 1× with cold PBS (plus Ca/Mg)/1% goat serum Add 1 ml conditioned media neat and incubate 90 min at room temp.

Wash plates 3× with PBS (plus Ca/Mg). On the 4th wash, add 1 ml 50% methanol to 1 ml PBS. Then add 1 ml methanol. Evacuate and add 1 ml methanol.

Wash 1× with PBS. Wash 1×PBS/1% goat serum.

Add secondary antibody (1-to-2,000 anti-human Fc conjugated to alkaline phosphatase (Jackson Lab)) in PBS/1% goat serum. Incubate 30–40 min room temp.

Wash 3× with PBS. Wash 1× alkaline phosphatase buffer (100 mM Tris-Cl, pH 9.5, 100 mM NaCl, 5 mM $MgCl_2$. Prepare alkaline phosphatase reagents: 4.5 ul/ml NBT and 3.5 ul/ml BCIP (Gibco) in alkaline phosphatase buffer.

Incubate 10–30 min, quench with 20 mM EDTA in PBS. Cells that have bound Slit polypeptides are visible by the presence of a dark purple reaction product.

In parallel incubations, positive controls are provided by titrating Slit binding with serial dilutions of the mutant receptor conditioned medium.

IV. Results: Binding of Slit to Robo

Cell expressing mammalian Slit polypeptides were shown to bind Robo. No reactivity was observed with control COS cells or with receptor-expressing COS cells in the presence of the secondary antibody but in the absence of the Slit-Fc fusion. Binding was observed to receptor-expression cells using a construct in which a Slit polypeptide is fused directly to alkaline phosphatase, for which a secondary antibody is not required. Receptor deletion mutants titrate the Slit-Robo binding, serving as a positive control for inhibition assays.

Protocol for High Throughput Robo-Slit Binding Assay

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}P$ Robo polypeptide 10× stock: $10^{-8}$–$10^{-6}$ M "cold" Robo polypeptide specific Robo domain supplemented with 200,000–250,000 cpm of labeled Robo (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM $NaVO_3$ (Sigma #S-6508) in 10 ml of PBS.

Slit: $10^{-7}$–$10^{-5}$ M biotinylated Slit in PBS.

B. Preparation of Assay Plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}P$-Robo (20–25,000 cpm/0.1–10 pmoles/well=$10^{-9}$–$10^{-7}$M final conc).

Shake at 25° C. for 15 minutes.
Incubate additional 45 minutes at 25° C.
Add 40 μM biotinylated Slit (0.1–10 pmoles/40 ul in assay buffer)
Incubate 1 hour at room temperature.
Stop the reaction by washing 4 times with 200 μM PBS.
Add 150 μM scintillation cocktail.
Count in Topcount.

D. Controls for All Assays (Located on Each Plate)
  a. Non-specific binding
  b. Soluble (non-biotinylated Slit) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising at least one sequence selected from the group consisting of SEQ ID NOS:2–6, 8 and 10–14, or a subsequence thereof having at least 16 consecutive amino acids residues thereof and comprising one or more unboxed amino acid residues of the corresponding sequence in at least one table selected from the group consisting of Table 1 and Table 2.

2. An isolated polypeptide according to claim 1 comprising at least one sequence selected from the group consisting of SEQ ID NOS:2–6, 8 and 10–14, or a subsequence thereof having at least 64 consecutive amino acid residues thereof and comprising one or more unboxed amino acid residues of the corresponding sequence in at least one table selected from the group consisting of Table 1 and Table 2.

3. An isolated polypeptide comprising at least one sequence selected from the group consisting of SEQ ID NOS:2–6 and 8–14.

4. An isolated polypeptide according to claim 1 comprising at least one sequence selected from the group consisting of SEQ ID NOS:2–6, or a subsequence thereof having at least 16 consecutive amino acid residues thereof and comprising one or more unboxed amino acid residues of the corresponding sequence in at least one table selected from the group consisting of Table 1 and Table 2.

5. An isolated polypeptide according to claim 1 comprising SEQ ID NO:2, 3, 4, 5, or 6, or a subsequence thereof having at least 64 consecutive amino acid residues thereof and comprising one or more unboxed amino acid residues of the corresponding sequence in at least one table selected from the group consisting of Table 1 and Table 2.

6. An isolated polypeptide according to claim 1 comprising SEQ ID NO:2, or a subsequence thereof having at least 16 consecutive amino acid residues thereof and comprising one or more unboxed amino acid residues of the corresponding sequence in Table 2.

7. An isolated polypeptide according to claim 1 comprising SEQ ID NO:2, or a subsequence thereof having at least 64 consecutive amino acid residues thereof and comprising one or more unboxed amino acid residues of the corresponding sequence in Table 2.

8. An isolated polypeptide according to claim 1 comprising SEQ ID NO:2.

9. An isolated polypeptide according to claim 1, comprising at least one sequence selected from the group consisting of SEQ ID NO: 2, amino acid residues 1–10; SEQ ID NO: 2, amino acid residues 29–41; SEQ ID NO: 2, amino acid residues 75–87 SEQ ID NO: 2, amino acid residues 92–109; SEQ ID NO: 2, amino acid residues 132–141; SEQ ID NO: 2, amino acid residues 192–205; SEQ ID NO: 2, amino acid residues 228–269; SEQ ID NO: 2, amino acid residues 295–311; SEQ ID NO: 2, amino acid residues 316–330; SEQ ID NO: 2, amino acid residues 373–382; SEQ ID NO: 2, amino acid residues 403–422; SEQ ID NO: 2, amino acid residues 474–485 SEQ ID NO: 2, amino acid residues 561–576; SEQ ID NO: 2, amino acid residues 683–697; SEQ ID NO: 2, amino acid residues 768–777; SEQ ID NO: 2, amino acid residues 798–813; SEQ ID NO: 2, amino acid residues 882–894; SEQ ID NO: 2, amino acid residues 934–946; SEQ ID NO: 2, amino acid residues 1054–1067; SEQ ID NO: 2, amino acid residues 1181–1192; SEQ ID NO: 2, amino acid residues 1273–1299; SEQ ID NO: 2, amino acid residues 1384–1397; SEQ ID NO: 2, amino acid residues 1468–1477; SEQ ID NO: 2, amino acid residues 1508–1517.

10. An isolated polypeptide comprising at least one sequence selected from the group consisting of SEQ ID NOS:2–6 and 10–14, or a subsequence thereof having at least 16 consecutive amino acid residues thereof and comprising one or more unboxed amino acid residues of the corresponding sequence in at least one table selected from the group consisting of Table 1 and Table 2.

11. An isolated polypeptide according to claim 10 comprising at least one sequence selected from the group consisting of SEQ ID NOS:2–6 and 10–14, or a subsequence thereof having at least 64 consecutive amino acid residues thereof and comprising one or more unboxed amino acid residues of the corresponding sequence in at least one table selected from the group consisting of Table 1 and Table 2.

12. An isolated polypeptide according to claim 10 comprising at least one sequence selected from the group consisting of SEQ ID NOS:2–6 and 10–4.

13. A method of identifying agents which modulate the interaction of a Robo polypeptide and a Slit polypeptide which consists of the isolated polypeptide according to claim 1, said method comprising the steps of:
 combining the Robo polypeptide, the Slit polypeptide, and a candidate agent under conditions whereby, but for the presence of the agent, the Robo and Slit polypeptides engage in a first interaction, and
 determining a second interaction of the Robo and Slit polypeptides in the presence of the agent,
 wherein a difference between the first and second interactions indicates that the agent modulates the interaction of the Robo and Slit polypeptides.

14. A method of identifying agents which modulate the interaction of a Robo polypeptide and a Slit polypeptide which consists of the isolated polypeptide according to claim 2, said method comprising the steps of:
 combining the Robo polypeptide, the Slit polypeptide, and a candidate agent under conditions whereby, but for the presence of the agent, the Robo and Slit polypeptides engage in a first interaction, and
 determining a second interaction of the Robo and Slit polypeptides in the presence of the agent,
 wherein a difference between the first and second interactions indicates that the agent modulates the interaction of the Robo and Slit polypeptides.

15. A method of identifying agents which modulate the interaction of a Robo polypeptide and a Slit polypeptide which consists of the isolated polypeptide according to claim 5, said method comprising the steps of:
 combining the Robo polypeptide, the Slit polypeptide, and a candidate agent under conditions whereby, but for the presence of the agent, the Robo and Slit polypeptides engage in a first interaction, and
 determining a second interaction of the Robo and Slit polypeptides in the presence of the agent,
 wherein a difference between the first and second interactions indicates that the agent modulates the interaction of the Robo and Slit polypeptides.

16. A method of identifying agents which modulate the interaction of a Robo polypeptide and a Slit polypeptide which consists of the isolated polypeptide according to claim 7, said method comprising the steps of:
 combining the Robo polypeptide, the Slit polypeptide, and a candidate agent under conditions whereby, but for the presence of the agent, the Robo and Slit polypeptides engage in a first interaction, and
 determining a second interaction of the Robo and Slit polypeptides in the presence of the agent,
 wherein a difference between the first and second interactions indicates that the agent modulates the interaction of the Robo and Slit polypeptides.

17. A method of modulating the interaction of a Robo polypeptide and a Slit polypeptide which consists of the isolated polypeptide according to claim 1, said method comprising the steps of combining the Robo polypeptide, the Slit polypeptide, and a modulator under conditions whereby, but for the presence of the modulator, the Robo and Slit polypeptides engage in a first interaction, and whereby the Robo and Slit polypeptides engage in a second interaction different from the first interaction.

18. A method of modulating the interaction of a Robo polypeptide and a Slit polypeptide which consists of the isolated polypeptide according to claim 2, said method comprising the steps of combining the Robo polypeptide, the Slit polypeptide, and a modulator under conditions whereby, but for the presence of the modulator, the Robo and Slit polypeptides engage in a first interaction, and whereby the Robo and Slit polypeptides engage in a second interaction different from the first interaction.

19. A method of modulating the interaction of a Robo polypeptide and a Slit polypeptide which consists of the isolated polypeptide according to claim 5, said method comprising the steps of combining the Robo polypeptide, the Slit polypeptide, and a modulator under conditions whereby, but for the presence of the modulator, the Robo and Slit polypeptides engage in a first interaction, and whereby the Robo and Slit polypeptides engage in a second interaction different from the first interaction.

20. A method of modulating the interaction of a Robo polypeptide and a Slit polypeptide which consists of the isolated polypeptide according to claim 7, said method comprising the steps of combining the Robo polypeptide, the Slit polypeptide, and a modulator under conditions whereby, but for the presence of the modulator, the Robo and Slit polypeptides engage in a first interaction, and whereby the Robo and Slit polypeptides engage in a second interaction different from the first interaction.

21. A method according to claim 17, wherein the modulator is a fragment of the Robo or Slit polypeptide.

* * * * *

UNITED STATES PATENT AND TRADEMARK OFFICE
CERTIFICATE OF CORRECTION

PATENT NO. : 6,046,015
APPLICATION NO. : 09/191647
DATED : April 4, 2000
INVENTOR(S) : Corey S. Goodman et al.

Page 1 of 1

It is certified that error appears in the above-identified patent and that said Letters Patent is hereby corrected as shown below:

In column 1, delete lines 11-13 and insert therefor a new paragraph 2:

--This invention was made with government support under Grant Number NS18366 awarded by the National Institutes of Health. The government has certain rights in the invention.--

Signed and Sealed this

Eighteenth Day of August, 2009

David J. Kappos
*Director of the United States Patent and Trademark Office*

SEQUENCE LISTING

<160> NUMBER OF SEQ ID NOS: 14

<210> SEQ ID NO 1
<211> LENGTH: 4758
<212> TYPE: DNA
<213> ORGANISM: human
<220> FEATURE:
<221> NAME/KEY: CDS
<222> LOCATION: (1)..(4575)

<400> SEQUENCE: 1

```
atg cgc ggc gtt ggc tgg cag atg ctg tcc ctg tcg ctg ggg tta gtg      48
Met Arg Gly Val Gly Trp Gln Met Leu Ser Leu Ser Leu Gly Leu Val
 1               5                  10                  15 ctg gcg atc ctg aac aag gtg gca ccg cag gcg tgc ccg gcg cag tgc      96
Leu Ala Ile Leu Asn Lys Val Ala Pro Gln Ala Cys Pro Ala Gln Cys
             20                  25                  30 tct tgc tcg ggc agc aca gtg gac tgt cac ggg ctg gcg ctg cgc agc     144
Ser Cys Ser Gly Ser Thr Val Asp Cys His Gly Leu Ala Leu Arg Ser
         35                  40                  45 gtg ccc agg aat atc ccc cgc aac acc gag aga ctg gat tta aat gga     192
Val Pro Arg Asn Ile Pro Arg Asn Thr Glu Arg Leu Asp Leu Asn Gly
     50                  55                  60 aat aac atc aca aga att acg aag aca gat ttt gct ggt ctt aga cat     240
Asn Asn Ile Thr Arg Ile Thr Lys Thr Asp Phe Ala Gly Leu Arg His
 65                  70                  75                  80 cta aga gtt ctt cag ctt atg gag aat aag att agc acc att gaa aga     288
Leu Arg Val Leu Gln Leu Met Glu Asn Lys Ile Ser Thr Ile Glu Arg
                 85                  90                  95 gga gca ttc cag gat ctt aaa gaa cta gag aga ctg cgt tta aac aga     336
Gly Ala Phe Gln Asp Leu Lys Glu Leu Glu Arg Leu Arg Leu Asn Arg
            100                 105                 110 aat cac ctt cag ctg ttt cct gag ttg ctg ttt ctt ggg act gcg aag     384
Asn His Leu Gln Leu Phe Pro Glu Leu Leu Phe Leu Gly Thr Ala Lys
        115                 120                 125 cta tac agg ctt gat ctc agt gaa aac caa att cag gca atc cca agg     432
Leu Tyr Arg Leu Asp Leu Ser Glu Asn Gln Ile Gln Ala Ile Pro Arg
    130                 135                 140 aaa gct ttc cgt ggg gca gtt gac ata aaa aat ttg caa ctg gat tac     480
Lys Ala Phe Arg Gly Ala Val Asp Ile Lys Asn Leu Gln Leu Asp Tyr
145                 150                 155                 160 aac cag atc agc tgt att gaa gat ggg gca ttc agg gct ctc cgg gac     528
Asn Gln Ile Ser Cys Ile Glu Asp Gly Ala Phe Arg Ala Leu Arg Asp
                165                 170                 175 ctg gaa gtg ctc act ctc aac aat aac aac att act aga ctt tct gtg     576
Leu Glu Val Leu Thr Leu Asn Asn Asn Asn Ile Thr Arg Leu Ser Val
            180                 185                 190 gca agt ttc aac cat atg cct aaa ctt agg act ttt cga ctg cat tca     624
```

```
Ala Ser Phe Asn His Met Pro Lys Leu Arg Thr Phe Arg Leu His Ser
            195                 200                 205 aac aac ctg tat tgt gac tgc cac ctg gcc tgg ctc tcc gac tgg ctt        672
Asn Asn Leu Tyr Cys Asp Cys His Leu Ala Trp Leu Ser Asp Trp Leu
210                 215                 220 cgc aaa agg cct cgg gtt ggt ctg tac act cag tgt atg ggc ccc tcc        720
Arg Lys Arg Pro Arg Val Gly Leu Tyr Thr Gln Cys Met Gly Pro Ser
225                 230                 235                 240 cac ctg aga ggc cat aat gta gcc gag gtt caa aaa cga gaa ttt gtc        768
His Leu Arg Gly His Asn Val Ala Glu Val Gln Lys Arg Glu Phe Val
                245                 250                 255 tgc agt gat gag gaa gaa ggt cac cag tca ttt atg gct cct tct tgt        816
Cys Ser Asp Glu Glu Glu Gly His Gln Ser Phe Met Ala Pro Ser Cys
            260                 265                 270 agt gtt ttg cac tgc cct gcc gcc tgt acc tgt agc aac aat atc gta        864
Ser Val Leu His Cys Pro Ala Ala Cys Thr Cys Ser Asn Asn Ile Val
        275                 280                 285 gac tgt cgt ggg aaa ggt ctc act gag atc ccc aca aat ctt cca gag        912
Asp Cys Arg Gly Lys Gly Leu Thr Glu Ile Pro Thr Asn Leu Pro Glu
290                 295                 300 acc atc aca gaa ata cgt ttg gaa cag aac aca atc aaa gtc atc cct        960
Thr Ile Thr Glu Ile Arg Leu Glu Gln Asn Thr Ile Lys Val Ile Pro
305                 310                 315                 320 cct gga gct ttc tca cca tat aaa aag ctt aga cga att gac ctg agc       1008
Pro Gly Ala Phe Ser Pro Tyr Lys Lys Leu Arg Arg Ile Asp Leu Ser
                325                 330                 335 aat aat cag atc tct gaa ctt gca cca gat gct ttc caa gga cta cgc       1056
Asn Asn Gln Ile Ser Glu Leu Ala Pro Asp Ala Phe Gln Gly Leu Arg
            340                 345                 350 tct ctg aat tca ctt gtc ctc tat gga aat aaa atc aca gaa ctc ccc       1104
Ser Leu Asn Ser Leu Val Leu Tyr Gly Asn Lys Ile Thr Glu Leu Pro
        355                 360                 365 aaa agt tta ttt gaa gga ctg ttt tcc tta cag ctc cta tta ttg aat       1152
Lys Ser Leu Phe Glu Gly Leu Phe Ser Leu Gln Leu Leu Leu Leu Asn
370                 375                 380 gcc aac aag ata aac tgc ctt cgg gta gat gct ttt cag gat ctc cac       1200
Ala Asn Lys Ile Asn Cys Leu Arg Val Asp Ala Phe Gln Asp Leu His
385                 390                 395                 400 aac ttg aac ctt ctc tcc cta tat gac aac aag ctt cag acc atc gcc       1248
Asn Leu Asn Leu Leu Ser Leu Tyr Asp Asn Lys Leu Gln Thr Ile Ala
                405                 410                 415 aag ggg acc ttt tca cct ctt cgg gcc att caa act atg cat ttg gcc       1296
Lys Gly Thr Phe Ser Pro Leu Arg Ala Ile Gln Thr Met His Leu Ala
            420                 425                 430 cag aac ccc ttt att tgt gac tgc cat ctc aag tgg cta gcg gat tat       1344
Gln Asn Pro Phe Ile Cys Asp Cys His Leu Lys Trp Leu Ala Asp Tyr
        435                 440                 445 ctc cat acc aac ccg att gag acc agt ggt gcc cgt tgc acc agc ccc       1392
Leu His Thr Asn Pro Ile Glu Thr Ser Gly Ala Arg Cys Thr Ser Pro
    450                 455                 460 cgc cgc ctg gca aac aaa aga att gga cag atc aaa agc aag aaa ttc       1440
Arg Arg Leu Ala Asn Lys Arg Ile Gly Gln Ile Lys Ser Lys Lys Phe
465                 470                 475                 480 cgt tgt tca ggt aca gaa gat tat cga tca aaa tta agt gga gac tgc       1488
Arg Cys Ser Gly Thr Glu Asp Tyr Arg Ser Lys Leu Ser Gly Asp Cys
                485                 490                 495 ttt gcg gat ctg gct tgc cct gaa aag tgt cgc tgt gaa gga acc aca       1536
Phe Ala Asp Leu Ala Cys Pro Glu Lys Cys Arg Cys Glu Gly Thr Thr
            500                 505                 510
```

-continued

```
gta gat tgc tct aat caa aag ctc aac aaa atc ccg gag cac att ccc    1584
Val Asp Cys Ser Asn Gln Lys Leu Asn Lys Ile Pro Glu His Ile Pro
        515                 520                 525 cag tac act gca gag ttg cgt ctc aat aat aat gaa ttt acc gtg ttg    1632
Gln Tyr Thr Ala Glu Leu Arg Leu Asn Asn Asn Glu Phe Thr Val Leu
    530                 535                 540 gaa gcc aca gga atc ttt aag aaa ctt cct caa tta cgt aaa ata aac    1680
Glu Ala Thr Gly Ile Phe Lys Lys Leu Pro Gln Leu Arg Lys Ile Asn
545                 550                 555                 560 ttt agc aac aat aag atc aca gat att gag gag gga gca ttt gaa gga    1728
Phe Ser Asn Asn Lys Ile Thr Asp Ile Glu Glu Gly Ala Phe Glu Gly
                565                 570                 575 gca tct ggt gta aat gaa ata ctt ctt acg agt aat cgt ttg gaa aat    1776
Ala Ser Gly Val Asn Glu Ile Leu Leu Thr Ser Asn Arg Leu Glu Asn
            580                 585                 590 gtg cag cat aag atg ttc aag gga ttg gaa agc ctc aaa act ttg atg    1824
Val Gln His Lys Met Phe Lys Gly Leu Glu Ser Leu Lys Thr Leu Met
        595                 600                 605 ttg aga agc aat cga ata acc tgt gtg ggg aat gac agt ttc ata gga    1872
Leu Arg Ser Asn Arg Ile Thr Cys Val Gly Asn Asp Ser Phe Ile Gly
    610                 615                 620 ctc agt tct gtg cgt ttg ctt tct ttg tat gat aat caa att act aca    1920
Leu Ser Ser Val Arg Leu Leu Ser Leu Tyr Asp Asn Gln Ile Thr Thr
625                 630                 635                 640 gtt gca cca ggg gca ttt gat act ctc cat tct tta tct act cta aac    1968
Val Ala Pro Gly Ala Phe Asp Thr Leu His Ser Leu Ser Thr Leu Asn
                645                 650                 655 ctc ttg gcc aat cct ttt aac tgt aac tgc tac ctg gct tgg ttg gga    2016
Leu Leu Ala Asn Pro Phe Asn Cys Asn Cys Tyr Leu Ala Trp Leu Gly
            660                 665                 670 gag tgg ctg aga aag aag aga att gtc acg gga aat cct aga tgt caa    2064
Glu Trp Leu Arg Lys Lys Arg Ile Val Thr Gly Asn Pro Arg Cys Gln
        675                 680                 685 aaa cca tac ttc ctg aaa gaa ata ccc atc cag gat gtg gcc att cag    2112
Lys Pro Tyr Phe Leu Lys Glu Ile Pro Ile Gln Asp Val Ala Ile Gln
    690                 695                 700 gac ttc act tgt gat gac gga aat gat gac aat agt tgc tcc cca ctt    2160
Asp Phe Thr Cys Asp Asp Gly Asn Asp Asp Asn Ser Cys Ser Pro Leu
705                 710                 715                 720 tct cgc tgt cct act gaa tgt act tgc ttg gat aca gtc gtc cga tgt    2208
Ser Arg Cys Pro Thr Glu Cys Thr Cys Leu Asp Thr Val Val Arg Cys
                725                 730                 735 agc aac aag ggt ttg aag gtc ttg ccg aaa ggt att cca aga gat gtc    2256
Ser Asn Lys Gly Leu Lys Val Leu Pro Lys Gly Ile Pro Arg Asp Val
            740                 745                 750 aca gag ttg tat ctg gat gga aac caa ttt aca ctg gtt ccc aag gaa    2304
Thr Glu Leu Tyr Leu Asp Gly Asn Gln Phe Thr Leu Val Pro Lys Glu
        755                 760                 765 ctc tcc aac tac aaa cat tta aca ctt ata gac tta agt aac aac aga    2352
Leu Ser Asn Tyr Lys His Leu Thr Leu Ile Asp Leu Ser Asn Asn Arg
    770                 775                 780 ata agc acg ctt tct aat cag agc ttc agc aac atg acc cag ctc ctc    2400
Ile Ser Thr Leu Ser Asn Gln Ser Phe Ser Asn Met Thr Gln Leu Leu
785                 790                 795                 800 acc tta att ctt agt tac aac cgt ctg aga tgt att cct cct cgc acc    2448
Thr Leu Ile Leu Ser Tyr Asn Arg Leu Arg Cys Ile Pro Pro Arg Thr
                805                 810                 815 ttt gat gga tta aag tct ctt cga tta ctt tct cta cat gga aat gac    2496
Phe Asp Gly Leu Lys Ser Leu Arg Leu Leu Ser Leu His Gly Asn Asp
            820                 825                 830
```

```
att tct gtt gtg cct gaa ggt gct ttc aat gat ctt tct gca tta tca     2544
Ile Ser Val Val Pro Glu Gly Ala Phe Asn Asp Leu Ser Ala Leu Ser
        835                 840                 845 cat cta gca att gga gcc aac cct ctt tac tgt gat tgt aac atg cag     2592
His Leu Ala Ile Gly Ala Asn Pro Leu Tyr Cys Asp Cys Asn Met Gln
    850                 855                 860 tgg tta tcc gac tgg gtg aag tcg gaa tat aag gag cct gga att gct     2640
Trp Leu Ser Asp Trp Val Lys Ser Glu Tyr Lys Glu Pro Gly Ile Ala
865                 870                 875                 880 cgt tgt gct ggt cct gga gaa atg gca gat aaa ctt tta ctc aca act     2688
Arg Cys Ala Gly Pro Gly Glu Met Ala Asp Lys Leu Leu Leu Thr Thr
                    885                 890                 895 ccc tcc aaa aaa ttt acc tgt caa ggt cct gtg gat gtc aat att cta     2736
Pro Ser Lys Lys Phe Thr Cys Gln Gly Pro Val Asp Val Asn Ile Leu
            900                 905                 910 gct aag tgt aac ccc tgc cta tca aat ccg tgt aaa aat gat ggc aca     2784
Ala Lys Cys Asn Pro Cys Leu Ser Asn Pro Cys Lys Asn Asp Gly Thr
        915                 920                 925 tgt aat agt gat cca gtt gac ttt tac cga tgc acc tgt cca tat ggt     2832
Cys Asn Ser Asp Pro Val Asp Phe Tyr Arg Cys Thr Cys Pro Tyr Gly
    930                 935                 940 ttc aag ggg cag gac tgt gat gtc cca att cat gcc tgc atc agt aac     2880
Phe Lys Gly Gln Asp Cys Asp Val Pro Ile His Ala Cys Ile Ser Asn
945                 950                 955                 960 cca tgt aaa cat gga gga act tgc cac tta aag gaa gga gaa gaa gat     2928
Pro Cys Lys His Gly Gly Thr Cys His Leu Lys Glu Gly Glu Glu Asp
                    965                 970                 975 gga ttc tgg tgt att tgt gct gat gga ttt gaa gga gaa aat tgt gaa     2976
Gly Phe Trp Cys Ile Cys Ala Asp Gly Phe Glu Gly Glu Asn Cys Glu
            980                 985                 990 gtc aac gtt gat gat tgt gaa gat aat gac tgt gaa aat aat tct aca     3024
Val Asn Val Asp Asp Cys Glu Asp Asn Asp Cys Glu Asn Asn Ser Thr
        995                 1000                1005 tgt gtc gat ggc att aat aac tac aca tgc ctt tgc cca cct gag tat     3072
Cys Val Asp Gly Ile Asn Asn Tyr Thr Cys Leu Cys Pro Pro Glu Tyr
    1010                1015                1020 aca ggt gag ttg tgt gag gag aag ctg gac ttc tgt gcc cag gac ctg     3120
Thr Gly Glu Leu Cys Glu Glu Lys Leu Asp Phe Cys Ala Gln Asp Leu
1025                1030                1035                1040 aac ccc tgc cag cac gat tca aag tgc atc cta act cca aag gga ttc     3168
Asn Pro Cys Gln His Asp Ser Lys Cys Ile Leu Thr Pro Lys Gly Phe
                    1045                1050                1055 aaa tgt gac tgc aca cca ggg tac gta ggt gaa cac tgc gac atc gat     3216
Lys Cys Asp Cys Thr Pro Gly Tyr Val Gly Glu His Cys Asp Ile Asp
            1060                1065                1070 ttt gac gac tgc caa gac aac aag tgt aaa aac gga gcc cac tgc aca     3264
Phe Asp Asp Cys Gln Asp Asn Lys Cys Lys Asn Gly Ala His Cys Thr
        1075                1080                1085 gat gca gtg aac ggc tat acg tgc ata tgc ccc gaa ggt tac agt ggc     3312
Asp Ala Val Asn Gly Tyr Thr Cys Ile Cys Pro Glu Gly Tyr Ser Gly
    1090                1095                1100 ttg ttc tgt gag ttt tct cca ccc atg gtc ctc cct cgt acc agc ccc     3360
Leu Phe Cys Glu Phe Ser Pro Pro Met Val Leu Pro Arg Thr Ser Pro
1105                1110                1115                1120 tgt gat aat ttt gat tgt cag aat gga gct cag tgt atc gtc aga ata     3408
Cys Asp Asn Phe Asp Cys Gln Asn Gly Ala Gln Cys Ile Val Arg Ile
                    1125                1130                1135 aat gag cca ata tgt cag tgt ttg cct ggc tat cag gga gaa aag tgt     3456
Asn Glu Pro Ile Cys Gln Cys Leu Pro Gly Tyr Gln Gly Glu Lys Cys
```

-continued

```
          1140              1145              1150
gaa aaa ttg gtt agt gtg aat ttt ata aac aaa gag tct tat ctt cag     3504
Glu Lys Leu Val Ser Val Asn Phe Ile Asn Lys Glu Ser Tyr Leu Gln
        1155              1160              1165 att cct tca gcc aag gtt cgg cct cag acg aac ata aca ctt cag att     3552
Ile Pro Ser Ala Lys Val Arg Pro Gln Thr Asn Ile Thr Leu Gln Ile
    1170              1175              1180 gcc aca gat gaa gac agc gga atc ctc ctg tat aag ggt gac aaa gac     3600
Ala Thr Asp Glu Asp Ser Gly Ile Leu Leu Tyr Lys Gly Asp Lys Asp
1185              1190              1195              1200 cat atc gcg gta gaa ctc tat cgg ggg cgt gtt cgt gcc agc tat gac     3648
His Ile Ala Val Glu Leu Tyr Arg Gly Arg Val Arg Ala Ser Tyr Asp
            1205              1210              1215 acc ggc tct cat cca gct tct gcc att tac agt gtg gag aca atc aat     3696
Thr Gly Ser His Pro Ala Ser Ala Ile Tyr Ser Val Glu Thr Ile Asn
        1220              1225              1230 gat gga aac ttc cac att gtg gaa cta ctt gcc ttg gat cag agt ctc     3744
Asp Gly Asn Phe His Ile Val Glu Leu Leu Ala Leu Asp Gln Ser Leu
    1235              1240              1245 tct ttg tcc gtg gat ggt ggg aac ccc aaa atc atc act aac ttg tca     3792
Ser Leu Ser Val Asp Gly Gly Asn Pro Lys Ile Ile Thr Asn Leu Ser
1250              1255              1260 aag cag tcc act ctg aat ttt gac tct cca ctc tat gta gga ggc atg     3840
Lys Gln Ser Thr Leu Asn Phe Asp Ser Pro Leu Tyr Val Gly Gly Met
1265              1270              1275              1280 cca ggg aag agt aac gtg gca tct ctg cgc cag gcc cct ggg cag aac     3888
Pro Gly Lys Ser Asn Val Ala Ser Leu Arg Gln Ala Pro Gly Gln Asn
            1285              1290              1295 gga acc agc ttc cac ggc tgc atc cgg aac ctt tac atc aac agt gag     3936
Gly Thr Ser Phe His Gly Cys Ile Arg Asn Leu Tyr Ile Asn Ser Glu
        1300              1305              1310 ctg cag gac ttc cag aag gtg ccg atg caa aca ggc att ttg cct ggc     3984
Leu Gln Asp Phe Gln Lys Val Pro Met Gln Thr Gly Ile Leu Pro Gly
    1315              1320              1325 tgt gag cca tgc cac aag aag gtg tgt gcc cat ggc aca tgc cag ccc     4032
Cys Glu Pro Cys His Lys Lys Val Cys Ala His Gly Thr Cys Gln Pro
1330              1335              1340 agc agc cag gca ggc ttc acc tgc gag tgc cag gaa gga tgg atg ggg     4080
Ser Ser Gln Ala Gly Phe Thr Cys Glu Cys Gln Glu Gly Trp Met Gly
1345              1350              1355              1360 ccc ctc tgt gac caa cgg acc aat gac cct tgc ctt gga aat aaa tgc     4128
Pro Leu Cys Asp Gln Arg Thr Asn Asp Pro Cys Leu Gly Asn Lys Cys
            1365              1370              1375 gta cat ggc acc tgc ttg ccc atc aat gcg ttc tcc tac agc tgt aag     4176
Val His Gly Thr Cys Leu Pro Ile Asn Ala Phe Ser Tyr Ser Cys Lys
        1380              1385              1390 tgc ttg gag ggc cat gga ggt gtc ctc tgt gat gaa gag gag gat ctg     4224
Cys Leu Glu Gly His Gly Gly Val Leu Cys Asp Glu Glu Glu Asp Leu
    1395              1400              1405 ttt aac cca tgc cag gcg atc aag tgc aag cat ggg aag tgc agg ctt     4272
Phe Asn Pro Cys Gln Ala Ile Lys Cys Lys His Gly Lys Cys Arg Leu
1410              1415              1420 tca ggt ctg ggg cag ccc tac tgt gaa tgc agc agt gga tac acg ggg     4320
Ser Gly Leu Gly Gln Pro Tyr Cys Glu Cys Ser Ser Gly Tyr Thr Gly
1425              1430              1435              1440 gac agc tgt gat cga gaa atc tct tgt cga ggg gaa agg ata aga gat     4368
Asp Ser Cys Asp Arg Glu Ile Ser Cys Arg Gly Glu Arg Ile Arg Asp
            1445              1450              1455 tat tac caa aag cag cag ggc tat gct gct tgc caa aca acc aag aag     4416
```

-continued

```
Tyr Tyr Gln Lys Gln Gln Gly Tyr Ala Ala Cys Gln Thr Thr Lys Lys
            1460                1465                1470 gtg tcc cga tta gag tgc aga ggt ggg tgt gca gga ggg cag tgc tgt      4464
Val Ser Arg Leu Glu Cys Arg Gly Gly Cys Ala Gly Gly Gln Cys Cys
    1475                1480                1485 gga ccg ctg agg agc aag cgg cgg aaa tac tct ttc gaa tgc act gac      4512
Gly Pro Leu Arg Ser Lys Arg Arg Lys Tyr Ser Phe Glu Cys Thr Asp
1490                1495                1500 ggc tcc tcc ttt gtg gac gag gtt gag aaa gtg gtg aag tgc ggc tgt      4560
Gly Ser Ser Phe Val Asp Glu Val Glu Lys Val Val Lys Cys Gly Cys
1505                1510                1515                1520 acg agg tgt gtg tcc taaacacact cccggcagct ctgtctttgg aaaaggttgt      4615
Thr Arg Cys Val Ser
            1525 atacttcttg accatgtggg actaatgaat gcttcatagt ggaaatattt gaaatatatt    4675 gtaaataca gaacagactt atttttatta tgagaataaa gactttttt ctgcatttgg      4735 aaaaaaaaaa aaaaaaaact cga                                            4758

<210> SEQ ID NO 2
<211> LENGTH: 1525
<212> TYPE: PRT
<213> ORGANISM: human

<400> SEQUENCE: 2

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Lys Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
```

-continued

```
                245                 250                 255
Cys Ser Asp Glu Glu Gly His Gln Ser Phe Met Ala Pro Ser Cys
            260                 265                 270
Ser Val Leu His Cys Pro Ala Ala Cys Thr Cys Ser Asn Asn Ile Val
            275                 280                 285
Asp Cys Arg Gly Lys Gly Leu Thr Glu Ile Pro Thr Asn Leu Pro Glu
    290                 295                 300
Thr Ile Thr Glu Ile Arg Leu Glu Gln Asn Thr Ile Lys Val Ile Pro
305                 310                 315                 320
Pro Gly Ala Phe Ser Pro Tyr Lys Lys Leu Arg Arg Ile Asp Leu Ser
                325                 330                 335
Asn Asn Gln Ile Ser Glu Leu Ala Pro Asp Ala Phe Gln Gly Leu Arg
            340                 345                 350
Ser Leu Asn Ser Leu Val Leu Tyr Gly Asn Lys Ile Thr Glu Leu Pro
            355                 360                 365
Lys Ser Leu Phe Glu Gly Leu Phe Ser Leu Gln Leu Leu Leu Leu Asn
    370                 375                 380
Ala Asn Lys Ile Asn Cys Leu Arg Val Asp Ala Phe Gln Asp Leu His
385                 390                 395                 400
Asn Leu Asn Leu Leu Ser Leu Tyr Asp Asn Lys Leu Gln Thr Ile Ala
                405                 410                 415
Lys Gly Thr Phe Ser Pro Leu Arg Ala Ile Gln Thr Met His Leu Ala
            420                 425                 430
Gln Asn Pro Phe Ile Cys Asp Cys His Leu Lys Trp Leu Ala Asp Tyr
            435                 440                 445
Leu His Thr Asn Pro Ile Glu Thr Ser Gly Ala Arg Cys Thr Ser Pro
    450                 455                 460
Arg Arg Leu Ala Asn Lys Arg Ile Gly Gln Ile Lys Ser Lys Lys Phe
465                 470                 475                 480
Arg Cys Ser Gly Thr Glu Asp Tyr Arg Ser Lys Leu Ser Gly Asp Cys
                485                 490                 495
Phe Ala Asp Leu Ala Cys Pro Glu Lys Cys Arg Cys Glu Gly Thr Thr
            500                 505                 510
Val Asp Cys Ser Asn Gln Lys Leu Asn Lys Ile Pro Glu His Ile Pro
            515                 520                 525
Gln Tyr Thr Ala Glu Leu Arg Leu Asn Asn Glu Phe Thr Val Leu
    530                 535                 540
Glu Ala Thr Gly Ile Phe Lys Lys Leu Pro Gln Leu Arg Lys Ile Asn
545                 550                 555                 560
Phe Ser Asn Asn Lys Ile Thr Asp Ile Glu Glu Gly Ala Phe Glu Gly
                565                 570                 575
Ala Ser Gly Val Asn Glu Ile Leu Leu Thr Ser Asn Arg Leu Glu Asn
            580                 585                 590
Val Gln His Lys Met Phe Lys Gly Leu Glu Ser Leu Lys Thr Leu Met
            595                 600                 605
Leu Arg Ser Asn Arg Ile Thr Cys Val Gly Asn Asp Ser Phe Ile Gly
    610                 615                 620
Leu Ser Ser Val Arg Leu Leu Ser Leu Tyr Asp Asn Gln Ile Thr Thr
625                 630                 635                 640
Val Ala Pro Gly Ala Phe Asp Thr Leu His Ser Leu Ser Thr Leu Asn
                645                 650                 655
Leu Leu Ala Asn Pro Phe Asn Cys Asn Cys Tyr Leu Ala Trp Leu Gly
            660                 665                 670
```

-continued

```
Glu Trp Leu Arg Lys Lys Arg Ile Val Thr Gly Asn Pro Arg Cys Gln
            675                 680                 685

Lys Pro Tyr Phe Leu Lys Glu Ile Pro Ile Gln Asp Val Ala Ile Gln
690                 695                 700

Asp Phe Thr Cys Asp Asp Gly Asn Asp Asn Ser Cys Ser Pro Leu
705                 710                 715                 720

Ser Arg Cys Pro Thr Glu Cys Thr Cys Leu Asp Thr Val Val Arg Cys
                725                 730                 735

Ser Asn Lys Gly Leu Lys Val Leu Pro Lys Gly Ile Pro Arg Asp Val
            740                 745                 750

Thr Glu Leu Tyr Leu Asp Gly Asn Gln Phe Thr Leu Val Pro Lys Glu
            755                 760                 765

Leu Ser Asn Tyr Lys His Leu Thr Leu Ile Asp Leu Ser Asn Asn Arg
770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
                820                 825                 830

Ile Ser Val Val Pro Glu Gly Ala Phe Asn Asp Leu Ser Ala Leu Ser
835                 840                 845

His Leu Ala Ile Gly Ala Asn Pro Leu Tyr Cys Asp Cys Asn Met Gln
850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Val Asn Ile Leu
                900                 905                 910

Ala Lys Cys Asn Pro Cys Leu Ser Asn Pro Cys Lys Asn Asp Gly Thr
            915                 920                 925

Cys Asn Ser Asp Pro Val Asp Phe Tyr Arg Cys Thr Cys Pro Tyr Gly
            930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Glu Asp
                965                 970                 975

Gly Phe Trp Cys Ile Cys Ala Asp Gly Phe Glu Gly Glu Asn Cys Glu
                980                 985                 990

Val Asn Val Asp Asp Cys Glu Asp Asn Asp Cys Glu Asn Asn Ser Thr
            995                 1000                1005

Cys Val Asp Gly Ile Asn Asn Tyr Thr Cys Leu Cys Pro Pro Glu Tyr
    1010                1015                1020

Thr Gly Glu Leu Cys Glu Glu Lys Leu Asp Phe Cys Ala Gln Asp Leu
1025                1030                1035                1040

Asn Pro Cys Gln His Asp Ser Lys Cys Ile Leu Thr Pro Lys Gly Phe
                1045                1050                1055

Lys Cys Asp Cys Thr Pro Gly Tyr Val Gly Glu His Cys Asp Ile Asp
            1060                1065                1070

Phe Asp Asp Cys Gln Asp Asn Lys Cys Lys Asn Gly Ala His Cys Thr
            1075                1080                1085
```

-continued

Asp Ala Val Asn Gly Tyr Thr Cys Ile Cys Pro Glu Gly Tyr Ser Gly
1090                1095                1100

Leu Phe Cys Glu Phe Ser Pro Pro Met Val Leu Pro Arg Thr Ser Pro
1105                1110                1115                1120

Cys Asp Asn Phe Asp Cys Gln Asn Gly Ala Gln Cys Ile Val Arg Ile
           1125                1130                1135

Asn Glu Pro Ile Cys Gln Cys Leu Pro Gly Tyr Gln Gly Glu Lys Cys
       1140                1145                1150

Glu Lys Leu Val Ser Val Asn Phe Ile Asn Lys Glu Ser Tyr Leu Gln
   1155                1160                1165

Ile Pro Ser Ala Lys Val Arg Pro Gln Thr Asn Ile Thr Leu Gln Ile
1170                1175                1180

Ala Thr Asp Glu Asp Ser Gly Ile Leu Leu Tyr Lys Gly Asp Lys Asp
1185                1190                1195                1200

His Ile Ala Val Glu Leu Tyr Arg Gly Arg Val Arg Ala Ser Tyr Asp
           1205                1210                1215

Thr Gly Ser His Pro Ala Ser Ala Ile Tyr Ser Val Glu Thr Ile Asn
       1220                1225                1230

Asp Gly Asn Phe His Ile Val Glu Leu Leu Ala Leu Asp Gln Ser Leu
   1235                1240                1245

Ser Leu Ser Val Asp Gly Gly Asn Pro Lys Ile Ile Thr Asn Leu Ser
1250                1255                1260

Lys Gln Ser Thr Leu Asn Phe Asp Ser Pro Leu Tyr Val Gly Gly Met
1265                1270                1275                1280

Pro Gly Lys Ser Asn Val Ala Ser Leu Arg Gln Ala Pro Gly Gln Asn
           1285                1290                1295

Gly Thr Ser Phe His Gly Cys Ile Arg Asn Leu Tyr Ile Asn Ser Glu
       1300                1305                1310

Leu Gln Asp Phe Gln Lys Val Pro Met Gln Thr Gly Ile Leu Pro Gly
   1315                1320                1325

Cys Glu Pro Cys His Lys Lys Val Cys Ala His Gly Thr Cys Gln Pro
1330                1335                1340

Ser Ser Gln Ala Gly Phe Thr Cys Glu Cys Gln Glu Gly Trp Met Gly
1345                1350                1355                1360

Pro Leu Cys Asp Gln Arg Thr Asn Asp Pro Cys Leu Gly Asn Lys Cys
           1365                1370                1375

Val His Gly Thr Cys Leu Pro Ile Asn Ala Phe Ser Tyr Ser Cys Lys
       1380                1385                1390

Cys Leu Glu Gly His Gly Gly Val Leu Cys Asp Glu Glu Asp Leu
   1395                1400                1405

Phe Asn Pro Cys Gln Ala Ile Lys Cys Lys His Gly Lys Cys Arg Leu
1410                1415                1420

Ser Gly Leu Gly Gln Pro Tyr Cys Glu Cys Ser Ser Gly Tyr Thr Gly
1425                1430                1435                1440

Asp Ser Cys Asp Arg Glu Ile Ser Cys Arg Gly Glu Arg Ile Arg Asp
           1445                1450                1455

Tyr Tyr Gln Lys Gln Gln Gly Tyr Ala Ala Cys Gln Thr Thr Lys Lys
       1460                1465                1470

Val Ser Arg Leu Glu Cys Arg Gly Gly Cys Ala Gly Gly Gln Cys Cys
   1475                1480                1485

Gly Pro Leu Arg Ser Lys Arg Arg Lys Tyr Ser Phe Glu Cys Thr Asp
1490                1495                1500

Gly Ser Ser Phe Val Asp Glu Val Glu Lys Val Val Lys Cys Gly Cys

-continued

```
1505                1510                1515                1520

Thr Arg Cys Val Ser
                1525

<210> SEQ ID NO 3
<211> LENGTH: 105
<212> TYPE: PRT
<213> ORGANISM: human

<400> SEQUENCE: 3

Ser Pro Cys Thr Cys Ser Asn Asn Ile Val Asp Cys Arg Gly Lys Gly
 1               5                  10                  15

Leu Met Glu Ile Pro Ala Asn Leu Pro Glu Gly Ile Val Glu Ile Arg
             20                  25                  30

Leu Glu Gln Asn Ser Ile Lys Ala Ile Pro Ala Gly Ala Phe Thr Gln
         35                  40                  45

Tyr Lys Lys Leu Lys Arg Ile Asp Ile Ser Lys Asn Gln Ile Ser Asp
 50                  55                  60

Ile Ala Pro Asp Ala Phe Gln Gly Leu Lys Ser Leu Thr Ser Leu Val
 65                  70                  75                  80

Leu Tyr Gly Asn Lys Ile Thr Glu Ile Ala Lys Gly Leu Phe Asp Gly
                 85                  90                  95

Leu Val Ser Leu Gln Leu Leu Leu
            100                 105

<210> SEQ ID NO 4
<211> LENGTH: 138
<212> TYPE: PRT
<213> ORGANISM: human

<400> SEQUENCE: 4

Glu Gly Ala Phe Asn Gly Ala Ala Ser Val Gln Glu Leu Met Leu Thr
 1               5                  10                  15

Gly Asn Gln Leu Glu Thr Val His Gly Arg Gly Phe Arg Gly Gly Leu
             20                  25                  30

Ser Gly Leu Lys Thr Leu Met Leu Arg Ser Asn Leu Ile Gly Cys Val
         35                  40                  45

Ser Asn Asp Thr Phe Ala Gly Leu Ser Ser Val Arg Leu Leu Ser Leu
 50                  55                  60

Tyr Asp Asn Arg Ile Thr Thr Ile Thr Pro Gly Ala Phe Thr Thr Leu
 65                  70                  75                  80

Val Ser Leu Ser Thr Ile Asn Leu Leu Ser Asn Pro Phe Asn Cys Asn
                 85                  90                  95

Cys His Leu Gly Ala Gly Leu Gly Lys Trp Leu Arg Lys Arg Arg Ile
            100                 105                 110

Val Ser Gly Asn Pro Arg Cys Gln Lys Pro Phe Phe Leu Lys Glu Ile
        115                 120                 125

Pro Ile Gln Gly Val Gly His Pro Gly Ile
    130                 135

<210> SEQ ID NO 5
<211> LENGTH: 160
<212> TYPE: PRT
<213> ORGANISM: human

<400> SEQUENCE: 5

Trp Pro Arg Cys Glu Cys Met Pro Gly Tyr Ala Gly Asp Asn Cys Ser
```

-continued

```
                1               5                   10                  15
        Glu Asn Gln Asp Asp Cys Arg Asp His Arg Cys Gln Asn Gly Ala Gln
                        20                  25                  30

Cys Met Asp Glu Val Asn Ser Tyr Ser Cys Leu Cys Ala Glu Gly Tyr
                    35                  40                  45

Ser Gly Gln Leu Cys Glu Ile Pro Pro His Leu Pro Ala Pro Lys Ser
                50                  55                  60

Pro Cys Glu Gly Thr Glu Cys Gln Asn Gly Ala Asn Cys Val Asp Gln
        65                  70                  75                  80

Gly Asn Arg Pro Val Cys Gln Cys Leu Pro Gly Phe Gly Gly Pro Glu
                        85                  90                  95

Cys Glu Lys Leu Leu Ser Val Asn Phe Val Asp Arg Asp Thr Tyr Leu
                    100                 105                 110

Gln Phe Thr Asp Leu Gln Asn Trp Xaa Arg Xaa Asn Ile Thr Leu Gln
                115                 120                 125

Val Phe Thr Ala Glu Asp Asn Gly Ile Leu Leu Tyr Asn Gly Gly Asn
            130                 135                 140

Asp His Ile Ala Val Xaa Leu Tyr Xaa Gly His Val Arg Phe Ser Tyr
        145                 150                 155                 160

<210> SEQ ID NO 6
<211> LENGTH: 103
<212> TYPE: PRT
<213> ORGANISM: human

<400> SEQUENCE: 6

Gln Cys His Ile Ser Asp Gln Gly Glu Pro Tyr Cys Leu Cys Gln Pro
        1               5                   10                  15

Gly Phe Ser Gly Glu His Cys Gln Gln Glu Asn Pro Cys Leu Gly Gln
                    20                  25                  30

Val Val Arg Glu Val Ile Arg Arg Gln Lys Gly Tyr Ala Ser Cys Ala
                35                  40                  45

Thr Ala Ser Lys Val Pro Ile Met Glu Cys Arg Gly Gly Cys Gly Pro
                50                  55                  60

Gln Cys Cys Gln Pro Thr Arg Ser Lys Arg Arg Lys Tyr Val Phe Gln
        65                  70                  75                  80

Cys Thr Asp Gly Ser Ser Phe Val Glu Glu Val Glu Arg His Leu Glu
                        85                  90                  95

Cys Gly Cys Leu Ala Cys Ser
                    100

<210> SEQ ID NO 7
<211> LENGTH: 1480
<212> TYPE: PRT
<213> ORGANISM: Drosophila melanogaster

<400> SEQUENCE: 7

Met Ala Ala Pro Ser Arg Thr Thr Leu Met Pro Pro Pro Phe Arg Leu
        1               5                   10                  15

Gln Leu Arg Leu Leu Ile Leu Pro Ile Leu Leu Leu Arg His Asp
                    20                  25                  30

Ala Val His Ala Glu Pro Tyr Ser Gly Gly Phe Gly Ser Ser Ala Val
                35                  40                  45

Ser Ser Gly Gly Leu Gly Ser Val Gly Ile His Ile Pro Gly Gly Gly
                50                  55                  60

Val Gly Val Ile Thr Glu Ala Arg Cys Pro Arg Val Cys Ser Cys Thr
```

-continued

```
                65                  70                  75                  80
Gly Leu Asn Val Asp Cys Ser His Arg Gly Leu Thr Ser Val Pro Arg
                        85                  90                  95
Lys Ile Ser Ala Asp Val Glu Arg Leu Glu Leu Gln Gly Asn Asn Leu
                    100                 105                 110
Thr Val Ile Tyr Glu Thr Asp Phe Gln Arg Leu Thr Lys Leu Arg Met
                115                 120                 125
Leu Gln Leu Thr Asp Asn Gln Ile His Thr Ile Glu Arg Asn Ser Phe
            130                 135                 140
Gln Asp Leu Val Ser Leu Glu Arg Leu Asp Ile Ser Asn Asn Val Ile
145                 150                 155                 160
Thr Thr Val Gly Arg Arg Val Phe Lys Gly Ala Gln Ser Leu Arg Ser
                165                 170                 175
Leu Gln Leu Asp Asn Asn Gln Ile Thr Cys Leu Asp Glu His Ala Phe
                    180                 185                 190
Lys Gly Leu Val Glu Leu Glu Ile Leu Thr Leu Asn Asn Asn Asn Leu
                195                 200                 205
Thr Ser Leu Pro His Asn Ile Phe Gly Gly Leu Gly Arg Leu Arg Ala
            210                 215                 220
Leu Arg Leu Ser Asp Asn Pro Phe Ala Cys Asp Cys His Leu Ser Trp
225                 230                 235                 240
Leu Ser Arg Phe Leu Arg Ser Ala Thr Arg Leu Ala Pro Tyr Thr Arg
                245                 250                 255
Cys Gln Ser Pro Ser Gln Leu Lys Gly Gln Asn Val Ala Asp Leu His
                260                 265                 270
Asp Gln Glu Phe Lys Cys Ser Gly Leu Thr Glu His Ala Pro Met Glu
            275                 280                 285
Cys Gly Ala Glu Asn Ser Cys Pro His Pro Cys Arg Cys Ala Asp Gly
            290                 295                 300
Ile Val Asp Cys Arg Glu Lys Ser Leu Thr Ser Val Pro Val Thr Leu
305                 310                 315                 320
Pro Asp Asp Thr Thr Asp Val Arg Leu Glu Gln Asn Phe Ile Thr Glu
                325                 330                 335
Leu Pro Pro Lys Ser Phe Ser Ser Phe Arg Arg Leu Arg Arg Ile Asp
                340                 345                 350
Leu Ser Asn Asn Asn Ile Ser Arg Ile Ala His Asp Ala Leu Ser Gly
            355                 360                 365
Leu Lys Gln Leu Thr Thr Leu Val Leu Tyr Gly Asn Lys Ile Lys Asp
            370                 375                 380
Leu Pro Ser Gly Val Phe Lys Gly Leu Gly Ser Leu Arg Leu Leu Leu
385                 390                 395                 400
Leu Asn Ala Asn Glu Ile Ser Cys Ile Arg Lys Asp Ala Phe Arg Asp
                405                 410                 415
Leu His Ser Leu Ser Leu Leu Ser Leu Tyr Asp Asn Asn Ile Gln Ser
            420                 425                 430
Leu Ala Asn Gly Thr Phe Asp Ala Met Lys Ser Met Lys Thr Val His
            435                 440                 445
Leu Ala Lys Asn Pro Phe Ile Cys Asp Cys Asn Leu Arg Trp Leu Ala
            450                 455                 460
Asp Tyr Leu His Lys Asn Pro Ile Glu Thr Ser Gly Ala Arg Cys Glu
465                 470                 475                 480
Ser Pro Lys Arg Met His Arg Arg Ile Glu Ser Leu Arg Glu Glu
                485                 490                 495
```

-continued

```
Lys Phe Lys Cys Ser Trp Gly Glu Leu Arg Met Lys Leu Ser Gly Glu
            500                 505                 510

Cys Arg Met Asp Ser Asp Cys Pro Ala Met Cys His Cys Glu Gly Thr
            515                 520                 525

Thr Val Asp Cys Thr Gly Arg Arg Leu Lys Glu Ile Pro Arg Asp Ile
        530                 535                 540

Pro Leu His Thr Thr Glu Leu Leu Asn Asp Asn Glu Leu Gly Arg
545                 550                 555                 560

Ile Ser Ser Asp Gly Leu Phe Gly Arg Leu Pro His Leu Val Lys Leu
                565                 570                 575

Glu Leu Lys Arg Asn Gln Leu Thr Gly Ile Glu Pro Asn Ala Phe Glu
            580                 585                 590

Gly Ala Ser His Ile Gln Glu Leu Gln Leu Gly Glu Asn Lys Ile Lys
            595                 600                 605

Glu Ile Ser Asn Lys Met Phe Leu Gly Leu His Gln Leu Lys Thr Leu
            610                 615                 620

Asn Leu Tyr Asp Asn Gln Ile Ser Cys Val Met Pro Gly Ser Phe Glu
625                 630                 635                 640

His Leu Asn Ser Leu Thr Ser Leu Asn Leu Ala Ser Asn Pro Phe Asn
                645                 650                 655

Cys Asn Cys His Leu Ala Trp Phe Ala Glu Cys Val Arg Lys Lys Ser
                660                 665                 670

Leu Asn Gly Gly Ala Ala Arg Cys Gly Ala Pro Ser Lys Val Arg Asp
                675                 680                 685

Val Gln Ile Lys Asp Leu Pro His Ser Glu Phe Lys Cys Ser Ser Glu
            690                 695                 700

Asn Ser Glu Gly Cys Leu Gly Asp Gly Tyr Cys Pro Pro Ser Cys Thr
705                 710                 715                 720

Cys Thr Gly Thr Val Ala Cys Ser Arg Asn Gln Leu Lys Glu Ile
                725                 730                 735

Pro Arg Gly Ile Pro Ala Glu Thr Ser Glu Leu Tyr Leu Glu Ser Asn
                740                 745                 750

Glu Ile Glu Gln Ile His Tyr Glu Arg Ile Arg His Leu Arg Ser Leu
            755                 760                 765

Thr Arg Leu Asp Leu Ser Asn Asn Gln Ile Thr Ile Leu Ser Asn Tyr
770                 775                 780

Thr Phe Ala Asn Leu Thr Lys Leu Ser Thr Leu Ile Ile Ser Tyr Asn
785                 790                 795                 800

Lys Leu Gln Cys Leu Gln Arg His Ala Leu Ser Gly Leu Asn Asn Leu
                805                 810                 815

Arg Val Val Ser Leu His Gly Asn Arg Ile Ser Met Leu Pro Glu Gly
                820                 825                 830

Ser Phe Glu Asp Leu Lys Ser Leu Thr His Ile Ala Leu Gly Ser Asn
            835                 840                 845

Pro Leu Tyr Cys Asp Cys Gly Leu Lys Trp Phe Ser Asp Trp Ile Lys
            850                 855                 860

Leu Asp Tyr Val Glu Pro Gly Ile Ala Arg Cys Ala Glu Pro Glu Gln
865                 870                 875                 880

Met Lys Asp Lys Leu Ile Leu Ser Thr Pro Ser Ser Ser Phe Val Cys
                885                 890                 895

Arg Gly Arg Val Arg Asn Asp Ile Leu Ala Lys Cys Asn Ala Cys Phe
            900                 905                 910
```

-continued

```
Glu Gln Pro Cys Gln Asn Gln Ala Gln Cys Val Ala Leu Pro Gln Arg
            915                 920                 925
Glu Tyr Gln Cys Leu Cys Gln Pro Gly Tyr His Gly Lys His Cys Glu
        930                 935                 940
Phe Met Ile Asp Ala Cys Tyr Gly Asn Pro Cys Arg Asn Asn Ala Thr
945                 950                 955                 960
Cys Thr Val Leu Glu Glu Gly Arg Phe Ser Cys Gln Cys Ala Pro Gly
            965                 970                 975
Tyr Thr Gly Ala Arg Cys Glu Thr Asn Ile Asp Asp Cys Leu Gly Glu
        980                 985                 990
Ile Lys Cys Gln Asn Asn Ala Thr Cys Ile Asp Gly Val Glu Ser Tyr
            995                1000                1005
Lys Cys Glu Cys Gln Pro Gly Phe Ser Gly Glu Phe Cys Asp Thr Lys
    1010                1015                1020
Ile Gln Phe Cys Ser Pro Glu Phe Asn Pro Cys Ala Asn Gly Ala Lys
1025                1030                1035                1040
Cys Met Asp His Phe Thr His Tyr Ser Cys Asp Cys Gln Ala Gly Phe
            1045                1050                1055
His Gly Thr Asn Cys Thr Asp Asn Ile Asp Asp Cys Gln Asn His Met
        1060                1065                1070
Cys Gln Asn Gly Gly Thr Cys Val Asp Gly Ile Asn Asp Tyr Gln Cys
    1075                1080                1085
Arg Cys Pro Asp Asp Tyr Thr Gly Lys Tyr Cys Glu Gly His Asn Met
    1090                1095                1100
Ile Ser Met Met Tyr Pro Gln Thr Ser Pro Cys Gln Asn His Glu Cys
1105                1110                1115                1120
Lys His Gly Val Cys Phe Gln Pro Asn Ala Gln Gly Ser Asp Tyr Leu
        1125                1130                1135
Cys Arg Cys His Pro Gly Tyr Thr Gly Lys Trp Cys Glu Tyr Leu Thr
            1140                1145                1150
Ser Ile Ser Phe Val His Asn Asn Ser Phe Val Glu Leu Glu Pro Leu
        1155                1160                1165
Arg Thr Arg Pro Glu Ala Asn Val Thr Ile Val Phe Ser Ser Ala Glu
    1170                1175                1180
Gln Asn Gly Ile Leu Met Tyr Asp Gly Gln Asp Ala His Leu Ala Val
1185                1190                1195                1200
Glu Leu Phe Asn Gly Arg Ile Arg Val Ser Tyr Asp Val Gly Asn His
            1205                1210                1215
Pro Val Ser Thr Met Tyr Ser Phe Glu Met Val Ala Asp Gly Lys Tyr
        1220                1225                1230
His Ala Val Glu Leu Leu Ala Ile Lys Lys Asn Phe Thr Leu Arg Val
            1235                1240                1245
Asp Arg Gly Leu Ala Arg Ser Ile Ile Asn Glu Gly Ser Asn Asp Tyr
    1250                1255                1260
Leu Lys Leu Thr Thr Pro Met Phe Leu Gly Gly Leu Pro Val Asp Pro
1265                1270                1275                1280
Ala Gln Gln Ala Tyr Lys Asn Trp Gln Ile Arg Asn Leu Thr Ser Phe
            1285                1290                1295
Lys Gly Cys Met Lys Glu Val Trp Ile Asn His Lys Leu Val Asp Phe
        1300                1305                1310
Gly Asn Ala Gln Arg Gln Gln Lys Ile Thr Pro Gly Cys Ala Leu Leu
    1315                1320                1325
Glu Gly Glu Gln Gln Glu Glu Glu Asp Asp Glu Gln Asp Phe Met Asp
```

-continued

```
          1330                1335               1340

Glu Thr Pro His Ile Lys Glu Pro Val Asp Pro Cys Leu Glu Asn
1345                1350                1355                1360

Lys Cys Arg Arg Gly Ser Arg Cys Val Pro Asn Ser Asn Ala Arg Asp
            1365                1370                1375

Gly Tyr Gln Cys Lys Cys Lys His Gly Gln Arg Gly Arg Tyr Cys Asp
        1380                1385                1390

Gln Gly Glu Gly Ser Thr Glu Pro Pro Thr Val Thr Ala Ala Ser Thr
    1395                1400                1405

Cys Arg Lys Glu Gln Val Arg Glu Tyr Tyr Thr Glu Asn Asp Cys Arg
1410                1415                1420

Ser Arg Gln Pro Leu Lys Tyr Ala Lys Cys Val Gly Cys Gly Asn
1425                1430                1435                1440

Gln Cys Cys Ala Ala Lys Ile Val Arg Arg Arg Lys Val Arg Met Val
            1445                1450                1455

Cys Ser Asn Asn Arg Lys Tyr Ile Lys Asn Leu Asp Ile Val Arg Lys
        1460                1465                1470

Cys Gly Cys Thr Lys Lys Cys Tyr
    1475                1480

<210> SEQ ID NO 8
<211> LENGTH: 155
<212> TYPE: PRT
<213> ORGANISM: Caenorhabditis elegans

<400> SEQUENCE: 8

Arg Asn Pro Xaa Ile Cys Asp Cys Asn Leu Gln Trp Leu Ala Gln Ile
1               5                   10                  15

Asn Leu Gln Lys Asn Ile Glu Thr Ser Gly Ala Arg Cys Glu Gln Pro
            20                  25                  30

Lys Arg Leu Arg Lys Lys Phe Ala Thr Leu Pro Pro Asn Lys Phe
        35                  40                  45

Lys Cys Lys Gly Ser Glu Ser Phe Val Ser Met Tyr Ala Asp Ser Cys
    50                  55                  60

Phe Ile Asp Ser Ile Cys Pro Thr Gln Cys Asp Cys Tyr Gly Thr Thr
65                  70                  75                  80

Val Asp Cys Asn Lys Arg Gly Leu Asn Thr Ile Pro Thr Ser Ile Pro
                85                  90                  95

Arg Phe Ala Thr Gln Leu Leu Ser Gly Asn Asn Ile Ser Thr Val
            100                 105                 110

Asp Leu Asn Ser Asn Ile His Val Leu Glu Asn Leu Glu Xaa Leu Asp
        115                 120                 125

Leu Ser Asn Asn His Ile Thr Phe Ile Asn Asp Lys Ser Phe Glu Lys
    130                 135                 140

Leu Ser Lys Leu Arg Glu Leu Xaa Leu Asn Asp
145                 150                 155

<210> SEQ ID NO 9
<211> LENGTH: 735
<212> TYPE: PRT
<213> ORGANISM: Caenorhabditis elegans

<400> SEQUENCE: 9

Ser Asn Lys Asn Leu Thr Ser Phe Pro Ser Arg Ile Pro Phe Asp Thr
1               5                   10                  15

Thr Glu Leu Tyr Leu Asp Ala Asn Tyr Ile Asn Glu Ile Pro Ala His
```

-continued

```
            20                  25                  30
Asp Leu Asn Arg Leu Tyr Ser Leu Thr Lys Leu Asp Leu Ser His Asn
         35                  40                  45
Arg Leu Ile Ser Leu Glu Asn Asn Thr Phe Ser Asn Leu Thr Arg Leu
 50                  55                  60
Ser Thr Leu Ile Ile Ser Tyr Asn Lys Leu Arg Cys Leu Gln Pro Leu
 65                  70                  75                  80
Ala Phe Asn Gly Leu Asn Ala Leu Arg Ile Leu Ser Leu His Gly Asn
                 85                  90                  95
Asp Ile Ser Phe Leu Pro Gln Ser Ala Phe Ser Asn Leu Thr Ser Ile
                100                 105                 110
Thr His Ile Ala Val Gly Ser Asn Ser Leu Tyr Cys Asp Cys Asn Met
                115                 120                 125
Ala Trp Phe Ser Lys Trp Ile Lys Ser Lys Phe Ile Glu Ala Gly Ile
         130                 135                 140
Ala Arg Cys Glu Tyr Pro Asn Thr Val Ser Asn Gln Leu Leu Leu Thr
145                 150                 155                 160
Ala Gln Pro Tyr Gln Phe Thr Cys Asp Ser Lys Val Pro Thr Lys Leu
                165                 170                 175
Ala Thr Lys Cys Asp Leu Cys Leu Asn Ser Pro Cys Lys Asn Asn Ala
                180                 185                 190
Ile Cys Glu Thr Thr Ser Ser Arg Lys Tyr Thr Cys Asn Cys Thr Pro
         195                 200                 205
Gly Phe Tyr Gly Val His Cys Glu Asn Gln Ile Asp Ala Cys Tyr Gly
         210                 215                 220
Ser Pro Cys Leu Asn Asn Ala Thr Cys Lys Val Ala Gln Ala Gly Arg
225                 230                 235                 240
Phe Asn Cys Tyr Cys Asn Lys Gly Phe Glu Gly Asp Tyr Cys Glu Lys
                245                 250                 255
Asn Ile Asp Asp Cys Val Asn Ser Lys Cys Glu Asn Gly Gly Lys Cys
                260                 265                 270
Val Asp Leu Val Arg Phe Cys Ser Glu Glu Leu Lys Asn Phe Gln Ser
         275                 280                 285
Phe Gln Ile Asn Ser Tyr Arg Cys Asp Cys Pro Met Glu Tyr Glu Gly
         290                 295                 300
Lys His Cys Glu Asp Lys Leu Glu Tyr Cys Thr Lys Lys Leu Asn Pro
305                 310                 315                 320
Cys Glu Asn Asn Gly Lys Cys Ile Pro Ile Asn Gly Ser Tyr Ser Cys
                325                 330                 335
Met Cys Ser Pro Gly Phe Thr Gly Asn Asn Cys Glu Thr Asn Ile Asp
                340                 345                 350
Asp Cys Lys Asn Val Glu Cys Gln Asn Gly Gly Ser Cys Val Asp Gly
         355                 360                 365
Ile Leu Ser Tyr Asp Cys Leu Cys Arg Pro Gly Tyr Ala Gly Gln Tyr
         370                 375                 380
Cys Glu Ile Pro Pro Met Met Asp Met Glu Tyr Gln Lys Thr Asp Ala
385                 390                 395                 400
Cys Gln Gln Ser Ala Cys Gly Gln Gly Glu Cys Val Ala Ser Gln Asn
                405                 410                 415
Ser Ser Asp Phe Thr Cys Lys Cys His Glu Gly Phe Ser Gly Pro Ser
                420                 425                 430
Cys Asp Arg Gln Met Ser Val Gly Phe Lys Asn Pro Gly Ala Tyr Leu
         435                 440                 445
```

```
Ala Leu Asp Pro Leu Ala Ser Asp Gly Thr Ile Thr Met Thr Leu Arg
            450                 455                 460

Thr Thr Ser Lys Ile Gly Ile Leu Leu Tyr Tyr Gly Asp Asp His Phe
465                 470                 475                 480

Val Ser Ala Glu Leu Tyr Asp Gly Arg Val Lys Leu Val Tyr Tyr Ile
                485                 490                 495

Gly Asn Phe Pro Ala Ser His Met Tyr Ser Ser Val Lys Val Asn Asp
                500                 505                 510

Gly Leu Pro His Arg Ile Ser Ile Arg Thr Ser Glu Arg Lys Cys Phe
            515                 520                 525

Leu Gln Ile Asp Lys Asn Pro Val Gln Ile Val Glu Asn Ser Gly Lys
530                 535                 540

Ser Asp Gln Leu Ile Thr Lys Gly Lys Glu Met Leu Tyr Ile Gly Gly
545                 550                 555                 560

Leu Pro Ile Glu Lys Ser Gln Asp Ala Lys Arg Arg Phe His Val Lys
                565                 570                 575

Asn Ser Glu Ser Leu Lys Gly Cys Ile Ser Ser Ile Thr Ile Asn Glu
                580                 585                 590

Val Pro Ile Asn Leu Gln Gln Ala Leu Glu Asn Val Asn Thr Glu Gln
                595                 600                 605

Ser Cys Ser Ala Thr Val Asn Phe Cys Ala Gly Ile Asp Cys Gly Asn
            610                 615                 620

Gly Lys Cys Thr Asn Asn Ala Leu Ser Pro Lys Gly Tyr Met Cys Gln
625                 630                 635                 640

Cys Asp Ser His Phe Ser Gly Glu His Cys Asp Glu Lys Arg Ile Lys
                645                 650                 655

Cys Asp Lys Gln Lys Phe Arg Arg His His Ile Glu Asn Glu Cys Arg
                660                 665                 670

Ser Val Asp Arg Ile Lys Ile Ala Glu Cys Asn Gly Tyr Cys Gly Gly
            675                 680                 685

Glu Gln Asn Cys Cys Thr Ala Val Lys Lys Gln Arg Lys Val Lys
690                 695                 700

Met Ile Cys Lys Asn Gly Thr Thr Lys Ile Ser Thr Val His Ile Ile
705                 710                 715                 720

Arg Gln Cys Gln Cys Glu Pro Thr Lys Ser Val Leu Ser Glu Lys
                725                 730                 735

<210> SEQ ID NO 10
<211> LENGTH: 154
<212> TYPE: PRT
<213> ORGANISM: mouse

<400> SEQUENCE: 10

Asp Pro Leu Pro Val His His Arg Cys Glu Cys Met Leu Gly Tyr Thr
1               5                   10                  15

Gly Asp Asn Cys Ser Glu Asn Gln Asp Asp Cys Lys Asp His Lys Cys
                20                  25                  30

Gln Asn Gly Ala Gln Cys Val Asp Glu Val Asn Ser Tyr Ala Cys Leu
            35                  40                  45

Cys Val Glu Gly Tyr Ser Gly Gln Leu Cys Glu Ile Pro Pro Ala Pro
        50                  55                  60

Arg Ser Ser Cys Glu Gly Thr Glu Cys Gln Asn Gly Ala Asn Cys Val
65                  70                  75                  80

Asp Gln Gly Ser Arg Pro Val Cys Gln Cys Leu Pro Gly Phe Gly Gly
```

```
                        85                  90                  95

Pro Glu Cys Glu Lys Leu Leu Ser Val Asn Phe Val Asp Arg Asp Thr
            100                 105                 110

Tyr Leu Gln Phe Thr Asp Leu Gln Asn Trp Pro Arg Ala Asn Ile Thr
        115                 120                 125

Leu Gln Val Ser Thr Ala Glu Asp Asn Gly Ile Leu Leu Tyr Asn Gly
    130                 135                 140

Asp Asn Asp His Ile Ala Val Glu Leu Tyr
145                 150

<210> SEQ ID NO 11
<211> LENGTH: 110
<212> TYPE: PRT
<213> ORGANISM: mouse

<400> SEQUENCE: 11

Ala Phe Lys Cys His His Gly Gln Cys His Ile Ser Asp Arg Gly Glu
1               5                   10                  15

Pro Tyr Cys Leu Cys Gln Pro Gly Phe Ser Gly His His Cys Glu Gln
            20                  25                  30

Glu Asn Pro Cys Met Gly Glu Ile Val Arg Glu Ala Ile Arg Arg Gln
        35                  40                  45

Lys Asp Tyr Ala Ser Cys Ala Thr Ala Ser Lys Val Pro Ile Met Glu
    50                  55                  60

Cys Arg Gly Gly Cys Gly Thr Thr Cys Cys Gln Pro Ile Arg Ser Lys
65                  70                  75                  80

Arg Arg Lys Tyr Val Phe Gln Cys Thr Asp Gly Ser Ser Phe Val Glu
                85                  90                  95

Glu Val Glu Arg His Leu Glu Cys Gly Cys Arg Ala Cys Ser
            100                 105                 110

<210> SEQ ID NO 12
<211> LENGTH: 134
<212> TYPE: PRT
<213> ORGANISM: mouse

<400> SEQUENCE: 12

His Leu Arg Val Leu Gln Leu Met Glu Asn Arg Ile Ser Thr Ile Glu
1               5                   10                  15

Arg Gly Ala Phe Gln Asp Leu Lys Glu Leu Glu Arg Leu Arg Leu Asn
            20                  25                  30

Arg Asn Asn Leu Gln Leu Phe Pro Glu Leu Leu Phe Leu Gly Thr Ala
        35                  40                  45

Arg Leu Tyr Arg Leu Asp Leu Ser Glu Asn Gln Ile Gln Ala Ile Pro
    50                  55                  60

Arg Lys Ala Phe Arg Gly Ala Val Asp Ile Lys Asn Leu Gln Leu Asp
65                  70                  75                  80

Tyr Asn Gln Ile Ser Cys Ile Glu Asp Gly Ala Phe Arg Ala Leu Arg
                85                  90                  95

Asp Leu Glu Val Leu Thr Leu Asn Asn Asn Asn Ile Thr Arg Leu Ser
            100                 105                 110

Val Ala Ser Phe Asn His Met Pro Lys Leu Arg Thr Phe Arg Leu His
        115                 120                 125

Ser Asn Asn Leu Tyr Cys
    130
```

-continued

```
<210> SEQ ID NO 13
<211> LENGTH: 104
<212> TYPE: PRT
<213> ORGANISM: mouse

<400> SEQUENCE: 13
```

| | | | | | | | | | | | | | | | |
|---|---|---|---|---|---|---|---|---|---|---|---|---|---|---|---|
| Asn | Asp | Asp | Cys | Val | Gly | His | Lys | Cys | Arg | His | Gly | Ala | Gln | Cys | |
| 1 | | | | 5 | | | | 10 | | | | | 15 | | |
| Val | Asp | Glu | Val | Asn | Gly | Tyr | Thr | Cys | Ile | Cys | Pro | Gln | Gly | Phe | Ser |
| | | | 20 | | | | | 25 | | | | | 30 | | |
| Gly | Leu | Phe | Cys | Glu | His | Pro | Pro | Met | Val | Leu | Gln | Thr | Ser | | |
| | | 35 | | | | | 40 | | | | | 45 | | | |
| Pro | Cys | Asp | Gln | Tyr | Glu | Cys | Gln | Asn | Gly | Ala | Gln | Cys | Ile | Val | Val |
| | 50 | | | | | 55 | | | | | 60 | | | | |
| Gln | Gln | Glu | Pro | Thr | Cys | Arg | Cys | Pro | Pro | Gly | Phe | Ala | Gly | Pro | Arg |
| 65 | | | | | 70 | | | | | 75 | | | | | 80 |
| Cys | Glu | Lys | Leu | Ile | Thr | Val | Asn | Phe | Val | Gly | Lys | Asp | Ser | Tyr | Val |
| | | | | 85 | | | | | 90 | | | | | 95 | |
| Glu | Leu | Ala | Ser | Ala | Lys | Val | Arg | | | | | | | | |
| | | | 100 | | | | | | | | | | | | |

```
<210> SEQ ID NO 14
<211> LENGTH: 243
<212> TYPE: PRT
<213> ORGANISM: mouse

<400> SEQUENCE: 14
```

| | | | | | | | | | | | | | | | |
|---|---|---|---|---|---|---|---|---|---|---|---|---|---|---|---|
| Ile | Leu | Asp | Val | Ala | Ser | Leu | Arg | Gln | Ala | Pro | Gly | Glu | Asn | Gly | Thr |
| 1 | | | | 5 | | | | 10 | | | | | 15 | | |
| Ser | Phe | His | Gly | Cys | Ile | Arg | Asn | Leu | Tyr | Ile | Asn | Ser | Glu | Leu | Gln |
| | | | 20 | | | | | 25 | | | | | 30 | | |
| Asp | Phe | Arg | Lys | Met | Pro | Met | Gln | Thr | Gly | Ile | Leu | Pro | Gly | Cys | Glu |
| | | 35 | | | | | 40 | | | | | 45 | | | |
| Pro | Cys | His | Lys | Lys | Val | Cys | Ala | His | Gly | Cys | Cys | Gln | Pro | Ser | Ser |
| | 50 | | | | | 55 | | | | | 60 | | | | |
| Gln | Ser | Gly | Phe | Thr | Cys | Glu | Cys | Glu | Glu | Gly | Trp | Met | Gly | Pro | Leu |
| 65 | | | | | 70 | | | | | 75 | | | | | 80 |
| Cys | Asp | Gln | Arg | Thr | Asn | Asp | Pro | Cys | Leu | Gly | Asn | Lys | Cys | Val | His |
| | | | | 85 | | | | | 90 | | | | | 95 | |
| Gly | Thr | Cys | Leu | Pro | Ile | Asn | Ala | Phe | Ser | Tyr | Ser | Cys | Lys | Cys | Leu |
| | | | 100 | | | | | 105 | | | | | 110 | | |
| Glu | Gly | His | Gly | Gly | Val | Leu | Cys | Asp | Glu | Glu | Asp | Leu | Phe | Asn | |
| | | 115 | | | | | 120 | | | | | 125 | | | |
| Pro | Cys | Gln | Met | Ile | Lys | Cys | Lys | His | Gly | Lys | Cys | Arg | Leu | Ser | Gly |
| | 130 | | | | | 135 | | | | | 140 | | | | |
| Val | Gly | Gln | Pro | Tyr | Cys | Glu | Cys | Asn | Ser | Gly | Phe | Thr | Gly | Asp | Ser |
| 145 | | | | | 150 | | | | | 155 | | | | | 160 |
| Cys | Asp | Arg | Glu | Ile | Ser | Cys | Arg | Gly | Glu | Arg | Ile | Arg | Asp | Tyr | Tyr |
| | | | | 165 | | | | | 170 | | | | | 175 | |
| Gln | Lys | Gln | Gln | Gly | Tyr | Ala | Ala | Cys | Gln | Thr | Thr | Lys | Lys | Val | Ser |
| | | | 180 | | | | | 185 | | | | | 190 | | |
| Arg | Leu | Glu | Cys | Arg | Gly | Gly | Cys | Ala | Gly | Gly | Gln | Cys | Cys | Gly | Pro |
| | | 195 | | | | | 200 | | | | | 205 | | | |
| Leu | Arg | Ser | Lys | Arg | Arg | Lys | Tyr | Ser | Phe | Glu | Cys | Thr | Asp | Gly | Ser |
| | 210 | | | | | 215 | | | | | 220 | | | | |
| Ser | Phe | Val | Asp | Glu | Val | Glu | Lys | Val | Val | Lys | Cys | Gly | Cys | Ala | Arg |
| 225 | | | | | 230 | | | | | 235 | | | | | 240 |
| Cys | Ala | Ser | | | | | | | | | | | | | |